US008208759B2

(12) United States Patent
Carver et al.

(10) Patent No.: US 8,208,759 B2
(45) Date of Patent: Jun. 26, 2012

(54) LIGHT VALVE PROJECTION OF VISIBLE IMAGE CORRELATED WITH NON-VISIBLE IMAGE

(75) Inventors: Roger S. Carver, McKinney, TX (US); Leigh Ann Files, Richardson, TX (US); Duane Scott Dewald, Dallas, TX (US); Walter M. Duncan, Dallas, TX (US)

(73) Assignee: Texas Instruments Incorporated, Dallas, TX (US)

( * ) Notice: Subject to any disclaimer, the term of this patent is extended or adjusted under 35 U.S.C. 154(b) by 1197 days.

(21) Appl. No.: 11/956,532

(22) Filed: Dec. 14, 2007

(65) Prior Publication Data

US 2009/0060301 A1 Mar. 5, 2009

Related U.S. Application Data

(60) Provisional application No. 60/968,886, filed on Aug. 29, 2007.

(51) Int. Cl.
*G06K 9/00* (2006.01)
*G06K 9/32* (2006.01)
*A61N 5/06* (2006.01)
*G03B 21/28* (2006.01)

(52) U.S. Cl. ......... 382/294; 382/115; 382/128; 607/88; 607/94; 353/99

(58) Field of Classification Search ......... None
See application file for complete search history.

(56) References Cited

U.S. PATENT DOCUMENTS

| 4,908,876 | A  | * | 3/1990  | DeForest et al. | 382/261 |
|---|---|---|---|---|---|
| 5,969,754 | A  | * | 10/1999 | Zeman | 348/136 |
| 6,319,273 | B1 | * | 11/2001 | Chen et al. | 607/88 |
| 6,436,127 | B1 |   | 8/2002  | Anderson et al. | |
| 6,984,228 | B2 |   | 1/2006  | Anderson et al. | |
| 7,068,808 | B1 |   | 6/2006  | Prokoski | |
| 2004/0021831 | A1 | * | 2/2004 | Koide | 353/31 |
| 2005/0015120 | A1 | * | 1/2005 | Seibel et al. | 607/54 |
| 2005/0251230 | A1 | * | 11/2005 | MacKinnon et al. | 607/88 |
| 2006/0122515 | A1 |   | 6/2006 | Zeman et al. | |
| 2006/0289772 | A1 |   | 12/2006 | Johnson et al. | |
| 2007/0021807 | A1 | * | 1/2007 | Kurtz | 607/88 |

OTHER PUBLICATIONS

Lovhoiden et al. (Jan. 2003) "Commercialization of vein contrast enhancement." Proc. SPIE vol. 4958, pp. 189-200.*
Lovhoiden, G. (May 2004) "Design of a prototype vein enhancing illuminator." Ph.D. Dissertation, University of Tennessee.*
InFocus LP 290 Datasheet. (2001).*
Sentech STC-1000 Datasheet. (2004).*

* cited by examiner

*Primary Examiner* — Bhavesh Mehta
*Assistant Examiner* — Barry Drennan
(74) *Attorney, Agent, or Firm* — Warren L. Franz; Wade J. Brady, III; Frederick J. Telecky, Jr.

(57) ABSTRACT

An image system comprises a light valve and an image capturing unit. The light valve comprises an array of individually addressable pixels capable of generating an image. The image capturing unit comprises a detector having an array of detector pixels capable of capturing images. The detector pixels are correlated with the light valve pixels.

10 Claims, 16 Drawing Sheets ial application Ser. No. 60/968,886 to Carver filed Aug. 29, 2007, the subject matter of which is incorporated herein by reference in its entirety.

LIGHT VALVE PROJECTION OF VISIBLE IMAGE CORRELATED WITH NON-VISIBLE IMAGE

CROSS-REFERENCE TO RELATED APPLICATIONS

The present application claims priority from the provisional application Ser. No. 60/968,886 to Carver filed Aug. 29, 2007, the subject matter of which is incorporated herein by reference in its entirety.

TECHNICAL FIELD OF THE INVENTION

The present invention relates to the art of digital image processing, and more particularly to the art of capturing images and reproducing the captured images at desired locations.

BACKGROUND OF THE INVENTION

In many applications, it is desired to detect non-visible features and produce visible images of the non-visible features—typically onto surfaces that obscure the non-visible features. This can be useful in instances in which a viewer needs simultaneously to see a non-visible feature and the visible image of the non-visible feature. For example, it is useful to locate subcutaneous features, such as veins, tumors, nerves, bones, foreign objects when investigating a body part. Vein viewing systems have been developed to allow medical personnel to locate veins to administer injections and intravenous delivery of drugs and fluids. Likewise, the ability to view internal structures of objects such as vehicles, walls, or buildings without having to touch or open the objects is useful.

It is also useful in camouflaging or veiling visible features or objects. For example, wherein an object stands in front of a background and conceals a portion of the background, the object can be obscured or hidden by producing an image of the concealed portion of the background to the corresponding surface portion of the object. As a consequence, the produced image on the object's surface and the exposed portion of the background form a "continuous" background—resulting in a visual effect of object-hiding.

SUMMARY OF THE INVENTION

In view of the foregoing, disclosed herein is an image system capable of capturing images and producing the captured images at desired locations, and a method of using the same.

In one example, an image system is disclosed herein, where the system comprises a light valve comprising an array of individually addressable pixels; and an image capturing unit comprising a detector that comprises an array of pixels, wherein at least one detector pixel is correlated with at least one light valve pixel.

In another example, a method is disclosed herein, where the method comprises providing an image system that comprises a light valve and an image capturing unit that comprises a detector, wherein the light valve comprises an array of individually addressable pixels; and wherein the detector comprises an array of detector pixels; obtaining a correlation between the light valve pixels and the detector pixels; capturing an image using the detector pixels; and reproducing the captured image using the light valve pixels based on the obtained correlation and the captured image.

In yet another example, a method is disclosed herein wherein the method comprises: generating first light of a first waveband (or wavelength); illuminating an area comprising a feature to be investigated with the first light; generating a first image of the illuminated feature by a detector having an array of pixels using the first light; providing an array of light valve pixels, each pixel of which is correlated to a detector pixel; setting each light valve pixel to a state based on the correlation and the first image; and generating a second image using second light of a second waveband using the light valve pixels.

In still yet another example, a method of treating an affected area in a body portion of a patient or a mammal is disclosed herein. The method comprises: a) providing a light valve comprising an array of light valve pixels; and a detector comprising an array of detector pixels, wherein the light valve pixels are correlated with the detector pixels; b) capturing an image of the body portion comprising the affected area using the detector pixels; c) identifying at least one detector pixel that corresponds to the affected area in the captured image; d) identifying at least one light valve pixel that is correlated to the identified detector pixel; and e) directing a selected light treatment onto the affected area by said identified light valve pixel.

DETAILED DESCRIPTION OF EXAMPLES

Disclosed herein is an image system having both image capturing and image reproducing capabilities; and a method of using the image system. A non-visible feature obscured by an object can be captured by an image capturing device of the image system; and a light valve can produce a visible image of the non-visible feature at a desired location. Instead of producing a visible image at a desired location, the light valve can also be used for directing light beams onto a feature at a location based upon analyses of a captured image of the feature. This can be of particular importance in medical treatments, wherein the feature is the affected portion of an organism, and the light beam is light (e.g. ultraviolet light) that can be used for treating or curing the affected portion.

In the following, the image system and methods of using the same will be discussed in detail with reference to selected examples. It will be appreciated by those skilled in the art that the following discussion is for demonstration purpose, and should not be interpreted as a limitation. Other variations within the scope of this disclosure are also applicable.

Figure 1:
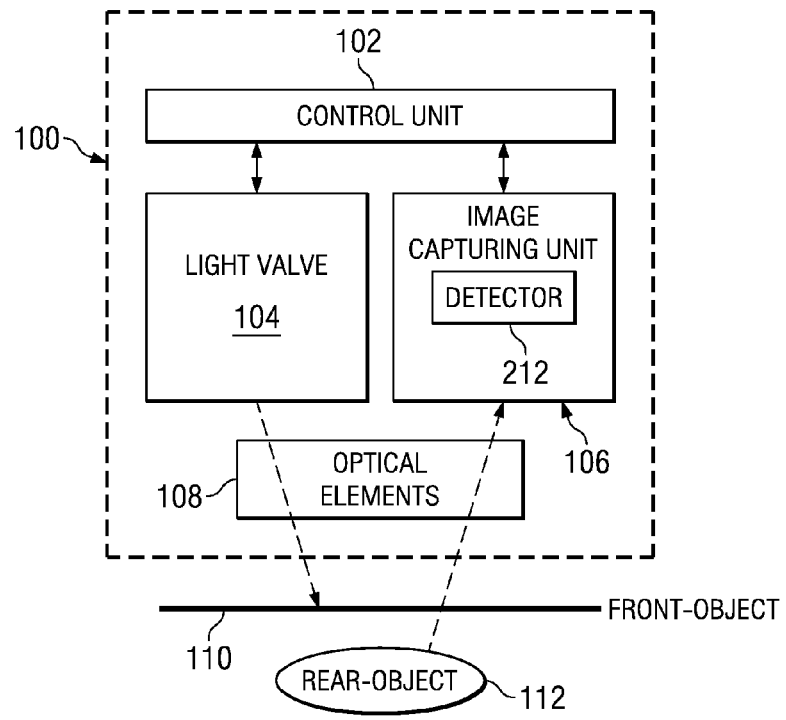
FIG. 1 is a block diagram schematically illustrates an exemplary image system capable of capturing images and reproducing the captured images at desired locations, wherein the image system comprises an image capturing unit for capturing images and a light valve for producing the captured images at desired locations.

Referring to the drawings, FIG. 1 schematically illustrates an exemplary image system having both image capturing and image reproducing abilities. In this example, image system 100 comprises control unit 102, light valve 104, image capturing unit 106, and optical elements 108.

Light valve 104 comprises an array of individually addressable pixels, such as a spatial light modulator (e.g. a deflectable and reflective micromirror-based spatial light modulator, a liquid-crystal display panel (LCD), a liquid-crystal-on-silicon (LCOS) based spatial light modulator, a silicon-crystal-reflective-display panel (sXRD), and an interferometric modulator (e.g. IMOD), etc.), and other types of light valves, such as self-light emitting light valves (e.g. organic light-emitting diode displays and plasma panels). In general, the light valve may have any desired native resolutions, wherein the native resolution is defined as the total number of light valve pixels in the active area of the light valve; and wherein the active area of a light valve is referred to as an area within which the light valve pixels are to be used for producing desired images. It is preferred (though not required) that the light valve has a native resolution substantially equal to or larger than the native resolution of the detector (212) of the image capturing unit (106) that is used for capturing images. As an example, the light valve may have a native resolution of 640×480 (VGA) or higher, such as 800×600 (SVGA) or higher, 1024×768 (XGA) or higher, 1280×1024 (SXGA) or higher, 1280×720 or higher, 1400×1050 or higher, 1600×1200 (UXGA) or higher, and 1920×1080 or higher, or integer multiples and fractions of these resolutions. Of course, other resolutions are also applicable depending upon the specific application. Each light valve pixel may have a characteristic dimension of 100 microns or less, such as 20 microns or less, and 10 microns or less, even though not required. The smallest distance between the adjacent light valve pixels, which is referred to as gap, can be 15 microns or less, 10 microns or less, and 5 microns or less. Of course, the light valve pixels can have other desired gap values. The center-to-center distance between the adjacent light valve pixels, which is referred to as pitch, can be 100 microns or less, 50 microns or less, and 10 microns or less, and more preferably from 15 microns to 4 microns, though other pitch values are also applicable. Even though FIG. 1 illustrates one light valve as an example, the image system (100) may comprise multiple light valves with the same or different light valve pixels and/or the same or different native resolutions. The multiple light valves can be integrated together to form a light valve assembly or can be disposed and used individually.

Image capturing unit 106 comprises detector 212. The detector comprises an array of pixels for capturing images. Examples of detector (212) are electronic charge-coupling-devices (CCDs), CMOS sensors, and other suitable image capturing devices. The detector (212) may have any desired native resolutions. As an example, the detector may have a native resolution of 640×480 (VGA) or higher, or integer multiples and fractions of these resolutions. Of course, other resolutions are also applicable. In some examples, an image capturing unit comprises one detector (e.g. a CCD or a CMOS sensor) of a particular resolution. In some other examples, an image capturing unit may comprise multiple detectors. Specifically, multiple detectors (with the same or different types of pixels and/or the same or different native resolutions) can be integrated together, such as integrated together so as to form a detector matrix. The integrated detectors can then be used as a single detector with desired resolution and performance. It is noted that different detectors may have different responses to incident light. Therefore, the detector of the system can be selected based upon the light used for capturing an image or images of an object.

Optical elements 108 comprises one or a set of optics for collecting and/or guiding light in image capturing and image producing. The optical elements may comprise standard optics, such as non-diffractive and transmissive lenses, specular folding mirrors, optical filters, and wave-plates. Alternatively, optical elements may comprise non-standard optics, such as diffractive optical elements (e.g. holographic optical elements with diffractive patterns) and non-specular reflective folding mirrors. It is noted that even illustrated in FIG. 1 that the optical elements are in one block, this is for demonstration purpose. The optical elements are deployed along the optical path(s) of the image system for imaging and/or image reproducing. Some exemplary optical arrangements will be demonstrated afterwards in FIG. 14 and FIG. 15.

Control unit 102 is provided for controlling operations of the components of the image system. For example, the control unit controls the image capturing unit (106) in capturing images; and controls the light valve (as well as other system components if necessary) in reproducing desired images. For reproducing images at desired locations, the control unit (102) further controls and maintains correlations between pixels of the light valve and pixels of the detector (212). In one example, correlations between the light valve and detector pixels can be maintained by the control unit as a look-up-table, wherein entries of the look-up table indicate the correlations between the light valve and detector pixels. The control unit can also be used, when necessary, for synchronizing the operations (e.g. image capturing and image reproducing) of the light valve and the image capturing unit. In some examples when the image capturing unit is implemented to have the capability of analyzing captured images, the control unit can be used for controlling the image data analyses (even though not required).

The control unit may comprise other functional members, such as an image processing unit, a communication interface for communicating (wired and/or wireless) with peripheral devices, a movable and/or non-movable storage, a buffer, a central-processing-unit (CPU), and a digital-signal-processing (DSP) unit. The image processing unit, when provided, can be a standard or customized device for processing image data. For example, an image processing unit may comprise a formatter that is capable of converting image data into converted data (e.g. bitplane data) that can be used by the light valve pixels. The control unit may comprise other components that are commonly used in existing digital image capturing devices (e.g. digital cameras and digital camcorders), and components that are commonly used in digital image processing instruments (e.g. image display systems using individually addressable pixels).

The control unit, as well as the functional members of the control unit, can be implemented as a software module comprising a set of computer-executable instructions and stored in a storage medium. Alternatively, the control unit can be implemented as a dedicated electronic device, such as an application-specific-integrated-circuit (ASIC) based chip or a field-programmable-gate-array (FPGA) based chip. When the control unit is implemented as an electronic device, such electronic device can be integrated with either one or both of the light valve and the detector. For example, the control unit in the form of an electronic device, and/or the detector, and/or the light valve can be integrated on single printed circuit board.

The image system (100) can be used for a wide range of applications. In one example, the image system can be used for reproducing visible images of non-visible features of objects at desired locations. A non-visible feature (or object) is a feature or (object) that is not observable using visible light from a certain observation direction. The invisibility of a non-visible object may be due to the object under test being concealed or veiled by another or other objects. For example, a non-visible object can be subcutaneous features, such as veins, tumors, nerves, bones, foreign objects of a body part (e.g. arm), or can be internal body organs, such as livers and prostates. These non-visible features are concealed or veiled by body skins. In another example, a non-visible object can be a structure embedded within or positioned behind a wall of a building. In the above, as well as other similar examples, the image system (100) can be used to generate an image of the non-visible feature or object; and reproduce a visible image of the non-visible feature object at a desired location, such as a surface of the non-visible object such that the non-visible object can be visualized by human eyes or other image detecting systems using visible light.

The invisibility of a non-visible object may alternatively be due to the non-visible object being positioned behind of another or other front objects such that the non-visible object is not observable using visible light from a certain angle. As an example wherein a person stands in front of a wall, a portion of the wall is thus concealed by the front standing person. In this instance, however, instead of visualizing the concealed portion of the wall, the person can be camouflaged using the image system (100) by reproducing the concealed portion of the wall (background) onto the surface of the front-standing person. In this instance, rear-object 112 in FIG. 1 can be a background object (e.g. wall of a building); while front-object 110 is the object to be camouflaged.

For capturing and reproducing the captured images at desired locations, pixels of the detector (212) of the image capturing unit and pixels of the light valve (104) are correlated. Specifically, a pixel of one device (e.g. the detector or light valve) can be correlated to one or a group of pixels of another device (e.g. the light valve or detector). A group of pixels of one device (e.g. the detector or light valve) can be correlated to a group of pixels of another device (e.g. the light valve or detector). Operational states (binary or non-binary) of the correlated pixels (or groups of pixels) can be dependent. Specifically, the operational states (binary or non-binary) of a light valve in producing a captured image can be dependent upon or can be determined by the state(s) of the correlated detector pixel(s) in capturing the image.

It is appreciated by those skilled in the art that pixel correlation is a feature of the image system (100) and is important in some applications. However, this feature is not an absolute requirement for some other applications. In other words, the image system (100) can also be used for image capturing and image reproducing without employing the pixel correlation feature in some other applications. For example, the image system (100) can be used as a standard image capturing instrument (e.g. a camera or a camcorder) and/or a standard image producing instrument (e.g. an image projector).

Figure 2:
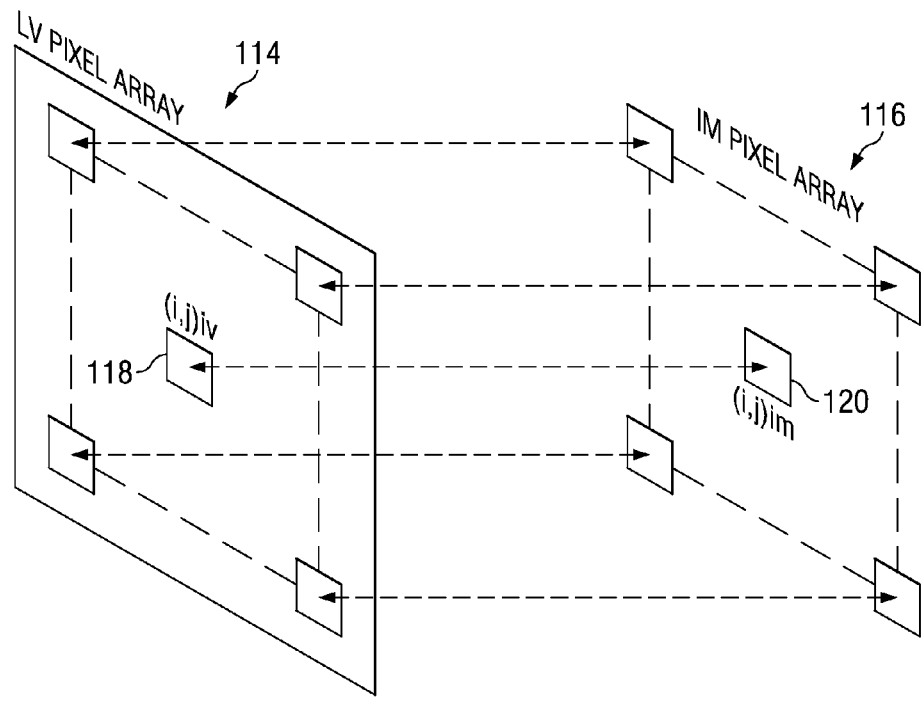
FIG. 2 schematically illustrates an exemplary pixel mapping scheme wherein a pixel of the light valve is correlated with a pixel of the image detector of the image capturing unit in the image system.

Pixels of the detector in the image capturing unit and pixels of the light valve can be correlated in a wide range of different ways, which will be discussed with reference to particular examples wherein single light valve and single detector are employed in an image system. However, the correlation schemes and methods of obtaining the correlation schemes as will be discussed in the following can be implemented for image systems with other configurations. For example, wherein the image system comprises multiple light valves and multiple detectors, light valves can be correlated with the detectors individually. In this instance, correlations of different light valves to different detectors may or may not comply with the same correlation scheme. Alternatively, the multiple light valves (or the multiple detectors) can be treated as an integrated light valve (or integrated detector). In one example, each detector pixel is correlated with one light valve pixel when the detector has a native resolution that is equal to or less than the native resolution of the light valve, or each light valve pixel is correlated with a detector pixel when the light valve resolution is less than the resolution of the detector, as schematically illustrated in FIG. 2. This unitary pixel-to-pixel mapping scheme can be especially useful when the light valve and the detector have substantially the same resolution, or when the light valve pixels and the detector pixels have substantially the same physical profile. Specifically, the light valve pixels have substantially the same dimension and pitch as the detector pixels.

Figure 3:
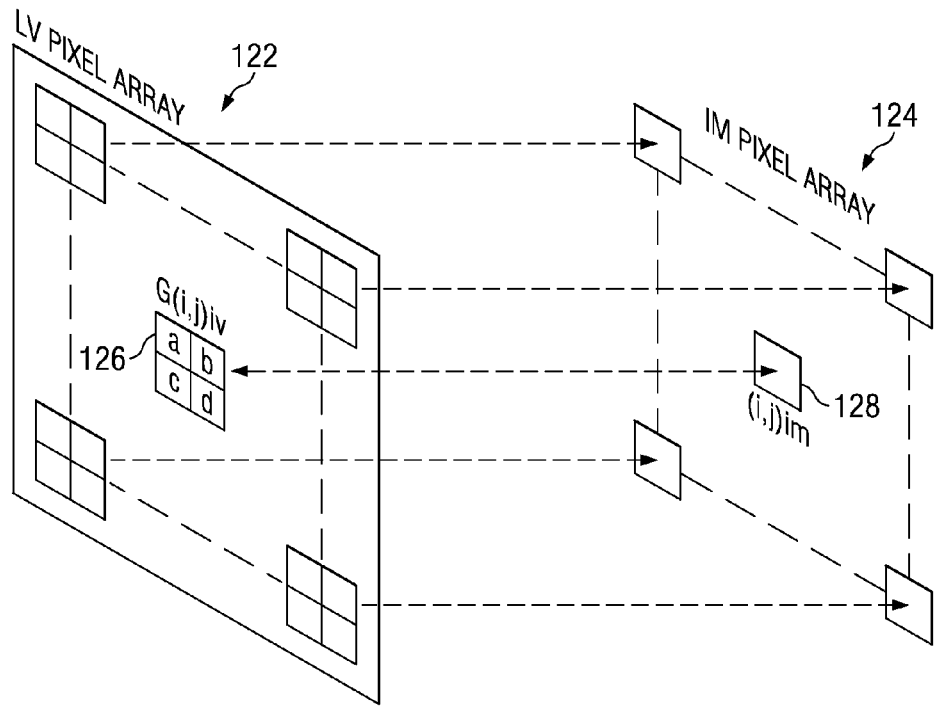
FIG. 3 schematically illustrates another exemplary pixel mapping scheme wherein a group of pixels of the light valve is correlated with one pixel of the image detector of the image capturing unit in the image system.

Referring to FIG. 2, the light valve comprises an array of light valve pixels 114; and the detector comprises an array of detector pixels 116. Each detector pixel, such as pixel $(i, j)_{im}$ 120 is correlated to a light valve pixel, such as light valve pixel $(i, j)_{lv}$ 118. If the light valve has a higher native resolution than the detector, a sub-array of the light valve pixels can be correlated with the detector pixels. This correlated sub-array of light valve pixels can be located at any desired position within the entire light valve pixel array, such as the center of the entire light valve pixel array or in the vicinity of an edge or a corner of the entire light valve pixel array. The remaining light valve pixels may or may not be correlated to detector pixels. In one example where the light valve has a resolution that is an integer multiple of the detector resolution, the entire light valve pixel array can be divided into sub-arrays with each sub-array having a native resolution substantially equal to the resolution of the detector. Each sub-array of the light valve can then be individually correlated to the pixels of the detector. Alternatively, each detector pixel can be correlated to a group of light valve pixels as schematically illustrated in FIG. 3. It is noted that the pixel mapping scheme as will be discussed in the following with reference to FIG. 3 is also applicable to other instances wherein the pixel arrays of the detector and light valve do not have matching physical profiles. For example, the light valve pixels and the detector pixels can have different characteristic dimensions, gaps, and/or pitches.

Referring to FIG. 3, pixel array 124 is in the detector of the image capturing unit; and pixel array 122 is in the light valve. Each detector pixel, such as detector pixel $(i, j)_{im}$ 128, has a dimension that is substantially the dimension of a group of light valve pixels, such as light valve pixel group $G(i, j)_{lv}$ 126 that comprises, in this example, light valve pixels a, b, c, and d. Each detector pixel can then be correlated to a group of light valve pixels. For example, detector pixel $(i, j)_{im}$ 128 can be correlated to pixel group $G(i, j)_{lv}$ 126 of the light valve. By such correlation, operation states of light valve pixels a, b, c, and d in producing a captured image can be dependent from the state of detector pixel $(i, j)_{im}$ 128 in capturing the image.

It is noted that when a group of light valve pixels are correlated to one detector pixel, the group of light valve pixels can be set to operational states in producing a captured image such that the collective effect of the group of light valve pixels simulates the state of the correlated detector pixel(s) in capturing the image to be produced. For example, detector pixel $(i, j)_{im}$ is a "white" pixel in capturing an image, thus outputting the maximum current. For reproducing the captured image, the light valve pixels in the pixel group $G(i, j)_{lv}$ can be set to individual states such that the collective output light from the pixel group $G(i, j)_{lv}$ exhibits a "white" point on the display target. However, light valve pixels of the group $G(i, j)_{lv}$ may or may not all be set to the ON state (in a binary mode). One or more of the pixels in the group may be set to the OFF state when desired.

By correlating multiple light valve pixels with one detector pixel, the contrast ratio and/or the bit depth for representing the grayscales of the reproduced image can be increased.

When the physical profile of light valve pixel array matches the physical profile of the detector pixel array, the pixels can be correlated with the pixel mapping scheme as discussed above with reference to FIG. 2. As an alternative, the pixels can be correlated in an offset style, as schematically illustrated in FIG. 4.

Figure 4:
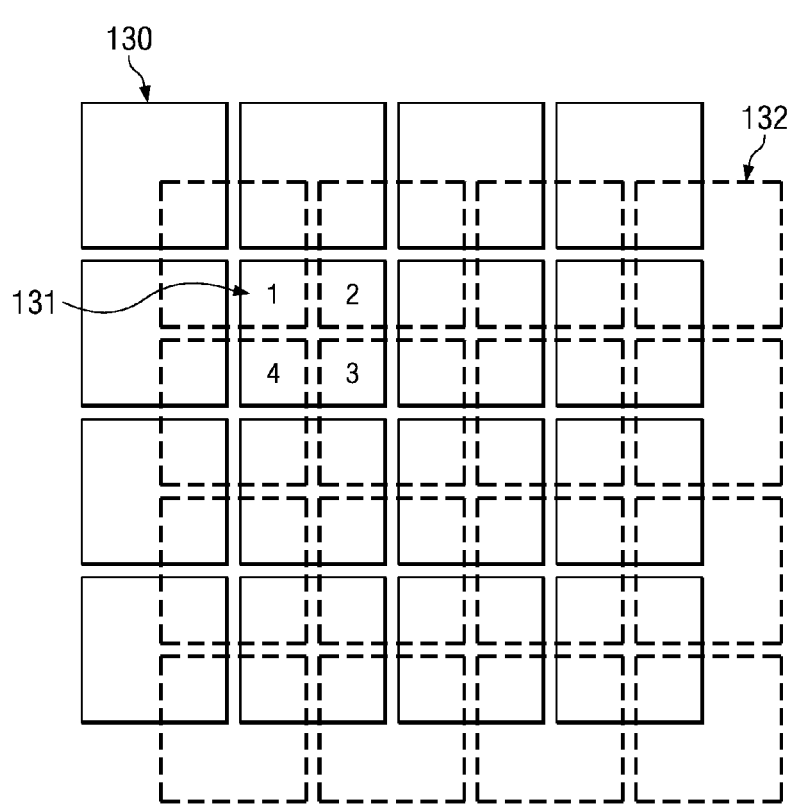
FIG. 4 schematically illustrates yet another exemplary pixel mapping scheme wherein a group of pixels of the light valve is correlated with a group of pixels of the image detector of the image capturing unit in the image system.

Referring to FIG. 4, pixel array 132 is in the light valve; and pixel array 130 is in the detector. The two pixel arrays have matching physical profiles. For mapping the pixels, the pixel array of the light valve (or the detector) can be displaced approximately half the diagonal length of a detector pixel (or a light valve) along the diagonal of the detector pixel array (or the light valve pixel array). As a consequence, each detector pixel can be correlated with four light valve pixels. For example, detector pixel 131 can be correlated to light valve pixels 1, 2, 3, and 4. In producing an image captured by the detector pixels (e.g. pixel 131), the operational states of the valve pixels (e.g. pixels 1, 2, 3, and 4) can be dependent or determined by the correlated detector pixels (e.g. pixel 131). By correlating multiple light valve pixels with one detector pixel, the contrast ratio and/or the bit depth for representing the grayscales of the reproduced image can be increased.

Figure 5:
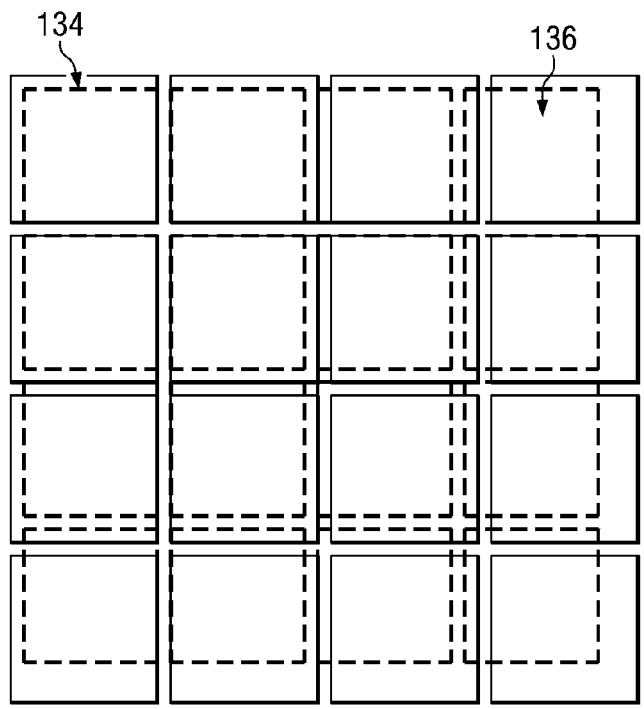
FIG. 5 schematically illustrates yet another exemplary pixel mapping scheme wherein a pixel of the light valve is correlated with one pixel of the image detector of the image capturing unit in the image system.

When the pixel array of one device (e.g. the light valve or the detector) has a physical profile that does not match the pixel array of another device (e.g. detector or the light valve), the pixel arrays of the two devices are referred to as non-matching pixel arrays. For example, a non-matching pixel array may have a different pixel dimension, pixel array pitch, and/or pixel gap from that of another non-matching pixel array. FIG. 5 schematically illustrates an exemplary pixel mapping scheme for non-matching pixel arrays.

Referring to FIG. 5, pixel array 134 is a light valve pixel array; and pixel array 136 is a detector pixel array. Pixels of detector array 136 are smaller than the light valve pixels. For example, the difference between the diagonals of the detector array and the light valve array is equal to or less than half diagonal of one light valve pixel. As a consequence, the area of the detector array is smaller than the area of the light vale pixel array; while the effective resolutions of the light valve pixels and the detector are substantially the same. In this example, each detector pixel can be correlated to a light valve pixel in the same way as described above with reference to FIG. 2.

Figure 6:
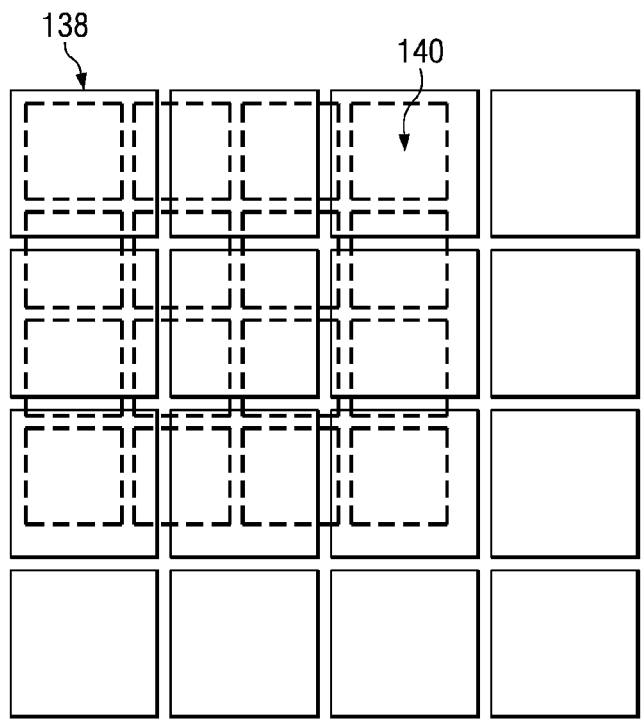
FIG. 6 schematically illustrates yet another exemplary pixel mapping scheme wherein a pixel of the light valve is correlated with one pixel of the image detector of the image capturing unit in the image system.

When pixel arrays of the light valve and detector have different dimensions, for example, when the difference between the diagonals of the light valve and detector arrays is larger than the diagonal of one light valve pixel, pixels of the light valve and the detector can be correlated by the effective pixels, as schematically illustrated in FIG. 6.

For demonstration purpose, the example in FIG. 6 assumes, without losing generality, that detector pixel array 140 and light valve pixel array 138 each have 4×4 pixels. Due to the smaller pixel size, the area of the detector pixel array is less than the area of the light valve pixel array; and the difference between the diagonals of the detector array and the light valve pixel array is larger than the diagonal of one light valve pixel. As a result, the detector pixel array has an area approximately corresponding to the area of a 3×3 sub-array of the light valve as schematically illustrated in FIG. 6. Pixels of the light valve and detector can be correlated by correlating each detector pixel with a light valve pixel in the effective 3×3 sub-array of the light valve. As such, some light valve pixels may be correlated to multiple detector pixels.

Figure 7:
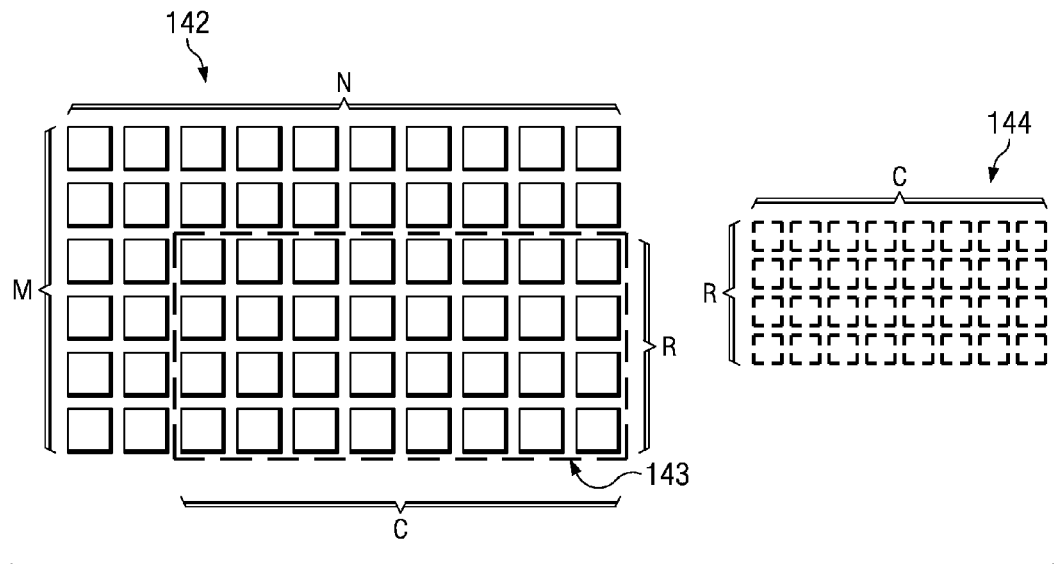
FIG. 7 schematically illustrates yet another exemplary pixel mapping scheme wherein an array of pixels of the light valve is correlated with an array of pixels of the image detector of the image capturing unit in the image system.

Alternative to the pixel mapping scheme as discussed above with reference to FIG. 6, non-matching pixel arrays of the light valve and the detector can be correlated on a resolution-basis, as schematically illustrate in FIG. 7.

Referring to FIG. 7, light valve pixel array 142 has a resolution of M rows and N columns, which can be written as M×N with M and N being integer numbers. Detector pixel array 144 has a resolution of R×C with R and C being integer numbers. Assuming the detector pixels are smaller than the light valve pixels, the detector array is smaller than the light valve array. Correlation of the two pixel array can be obtained by selecting a sub-array (e.g. sub-array 143) of light valve array 142 such that the selected sub-array (143) has a resolution substantially equal to the resolution of the detector pixel array. As illustrated in FIG. 7, the selected sub-array (143) has R rows and C columns. The detector array pixels can then be correlated to the pixels of the selected sub-array (143), for example, using the same pixel mapping scheme as discussed above with reference to FIG. 2 or FIG. 4.

Alternative to selecting a sub-array with a resolution substantially equal to the resolution of the detector pixel array, a sub-array can be selected such that the selected sub-array has a resolution that is an integer multiple of the detector pixel array. By way of example, the selected sub-array of the light vale can have a resolution of (p×R)×(q×C), while p and q are integers, and may or may not have the same value. Obviously, p and q should preferably have values such that (p×R) is equal to or less than M; and of (q×C) is equal to or less than M. Pixels of the detectors each can be correlated with multiple light valve pixels using a pixel mapping scheme as discussed above with reference to FIG. 4. Specifically, each detector pixel can be correlated to p×q light valve pixels.

In examples wherein multiple detectors, or multiple image capturing pixel arrays, are provided in an image system, each detector (or image capturing pixel array) can be independently correlated to a sub-array of the light valve pixel array. It is preferred that the sub-arrays correlated to different detectors (or image capturing pixel arrays) are substantially not overlapped. In an alternative example, multiple light valve pixel arrays can be provided with each light valve pixel array being correlated with a detector pixel array.

The pixel correlations as discussed above can be obtained in many ways. An exemplary method of correlating pixels of the detector and the light valve of the image system in FIG. 2 is shown in the flow chart in FIG. 8.

Figure 8:
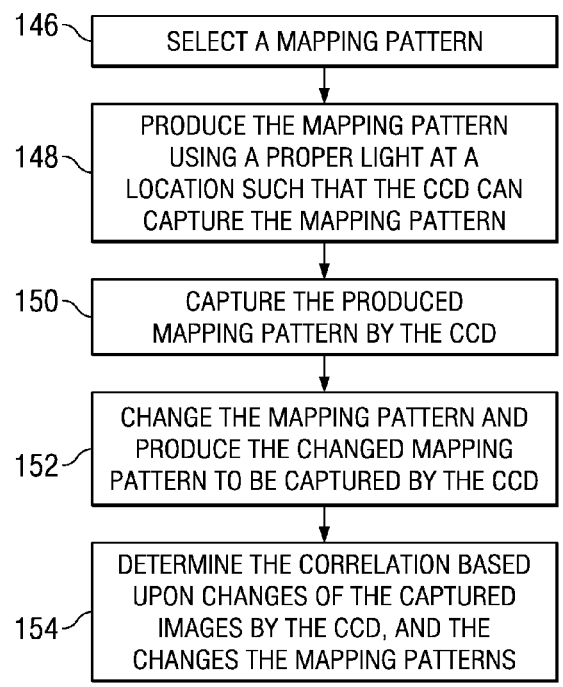
FIG. 8 is a flow chart showing the steps executed for performing an exemplary pixel mapping for correlating each pixel of the image detector of the image capturing device with a pixel of the light valve in the image system.

Referring to FIG. 8, a pixel mapping pattern is selected (step 146). A pixel mapping pattern is an image to be produced by the light valve and to be captured by the detector of the image capturing unit so as to correlate pixels of the detector with pixels of the light valve. The pixel mapping pattern can be implemented in a wide range of ways. In one example, a pixel mapping pattern can be a checkerboard. In another example, a pixel mapping pattern can be an image wherein all image pixels have the same state (e.g. white or black) except one image pixel at a given position (e.g. the pixel of (i, j)) being set to a different state (e.g. black or white) at different time periods.

The selected pixel mapping pattern is then produced by the light valve pixels at a location such that the produced pixel mapping pattern can be captured by the detector of the image capturing unit (step 148). The produced pixel mapping pattern is then captured by the detector pixels of the image capturing unit (step 150). When single pixel mapping pattern is sufficient for correlating detector pixels with light valve pixels, such as that will be discussed afterward with reference to FIG. 10, the correlation of the light valve pixels with the detector pixels is determined (step 154). Otherwise, the pixel mapping pattern is changed (step 152), for example, by selecting another pixel mapping pattern, producing the new pixel mapping pattern, and capturing the new pixel mapping pattern by the detector pixels. The above steps can be repeated as many times as needed until the correlation of the light valve pixels and detector pixels can be determined at step 154.

The pixel mapping method as described above with reference to FIG. 8 can be implemented in many ways depending upon the specific pixel mapping patterns selected. For demonstration purpose, selected exemplary implementations of the pixel mapping method as discussed above will be illustrated in the following with reference to FIG. 9 through FIG. 13. It will be appreciated by those skilled in the art that the following discussion is for demonstration purpose, and should not be interpreted as a limitation. Other variations are also applicable.

It is noted that detector pixels and the light valve pixels may be operable for light in different wavelength ranges. For example, the detector pixels may be operated for capturing non-visible light, such as infrared light; while the light valve pixels are operable for both visible and non-visible light (e.g. infrared light). In these examples, determination of the pixel correlation can be performed by using light that is operable for both light valve and the detector, such as infrared light.

Figure 9:
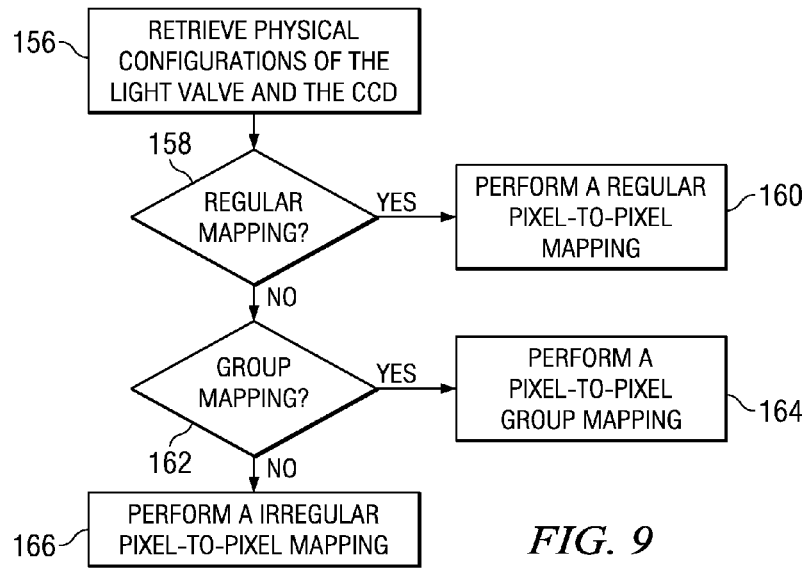
FIG. 9 is a flow chart showing the steps executed for performing another exemplary pixel mapping for correlating pixels of the image detector of the image capturing device with pixels of the light valve in the image system.

Referring to FIG. 9, physical configurations (or profiles) of the light valve pixel array and the detector pixel array can be retrieved (step 156). Based on the retrieved physical configurations of the pixel arrays, it is determined whether to apply a regular pixel mapping (step 158). For example, if the physical configurations of the light valve pixel array and the detector pixel array substantially match, a regular pixel-to-pixel mapping is performed (step 160). The regular pixel-to-pixel mapping can be performed in many ways, one of which is schematically illustrated in FIG. 10.

Figure 10:
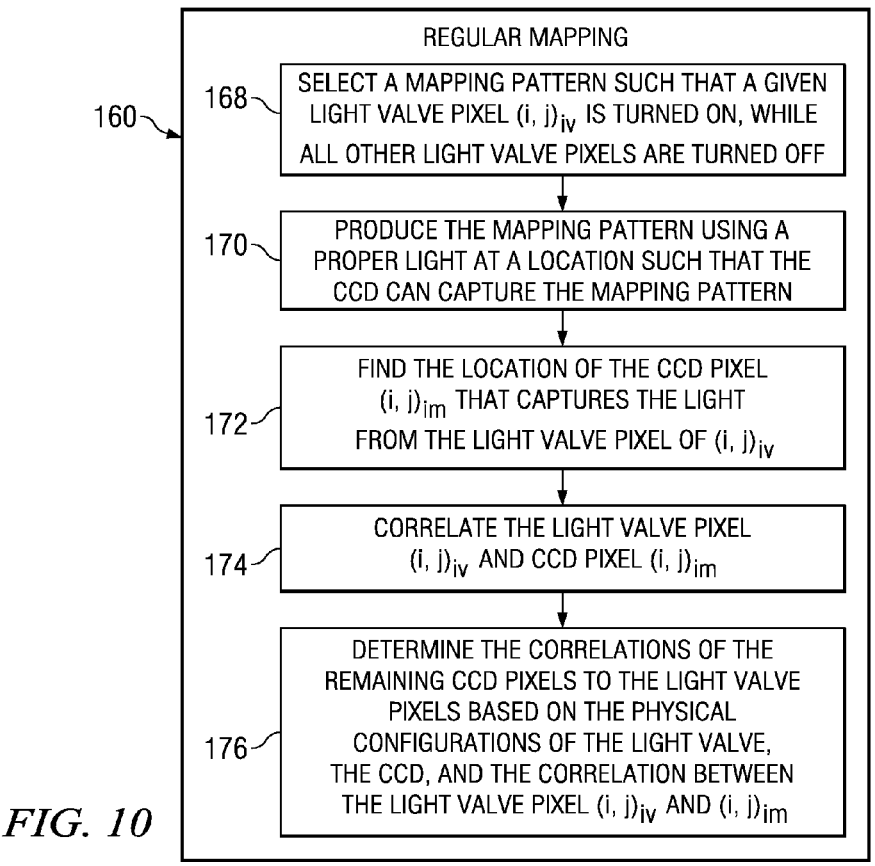
FIG. 10 is a flow chart showing the steps executed for performing an exemplary regular pixel mapping in the method of FIG. 9.

Referring to FIG. 10, a pixel mapping pattern is selected at step 168. The pixel mapping pattern in this example comprises one unique image pixel having a state that is different from all other image pixels. For example, image pixel at given location (i, j) can be set to "white" or ("black"); while all other image pixels are set to "black" or ("white"). For producing the selected pixel mapping pattern, the light valve pixel at location $(i, j)_{lv}$ is turned ON (for the white image pixel) or OFF (for the black image pixel) when the light valve pixels are operated at a binary mode. The pixel mapping pattern can then be produced by the light valve (step 170). The produced image is then captured by the detector pixels of the image capturing unit. Because the produced image has one unique image pixel that is white (or black) and all other image pixels are black (or white), one of the detector pixels detects an image pixel value different from other detector pixels (step 172); and this detector pixel (e.g. pixel $(i, j)_{im}$ can thus be correlated with the light valve pixel at location $((i, j)_{lv}$ (step 174). Based on the physical configurations of the light valve pixel array and the detector pixel array, and the correlation between light valve pixel $(i, j)_{lv}$ and detector pixel $(i, j)_{im}$, correlations between the remaining light valve pixels and detector pixels can thus be determined step 176).

Referring again to FIG. 9, if it is determined that a regular pixel mapping is not proper at step 158, it is further determined whether to perform a group mapping based upon the physical configurations of the light valve pixels and detector pixels (step 162). A group mapping can be proper when the physical configuration of the light valve pixel array substantially match the physical configuration of the detector pixel array, except that the detector pixels (or light valve pixels) each has a dimension that is substantially an integer multiple of a light valve pixel (or a detector pixel), such as that schematically illustrated in FIG. 3. If a group pixel mapping is proper by the determination at step 162, a group pixel mapping is performed at step 164. The group mapping can be performed in many ways, one of which is schematically illustrated in FIG. 11, wherein it is assumed, without losing generality, that each detector pixel is substantially 4 times in area of a light valve pixel, as schematically illustrated in FIG. 3.

Figure 11:
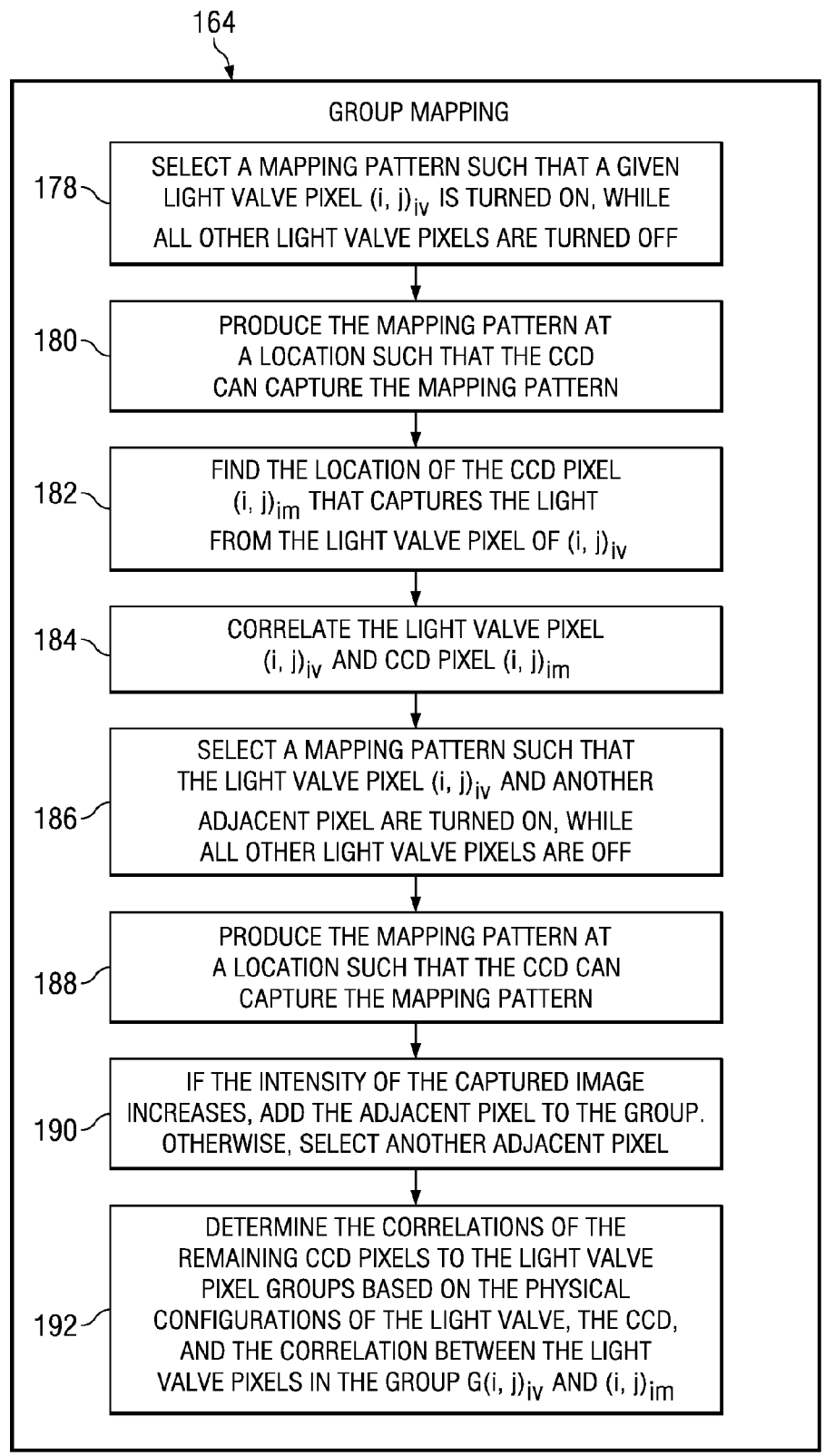
FIG. 11 is a flow chart showing the steps executed for performing an exemplary group pixels mapping in the method of FIG. 9.

Referring to FIG. 11 and as with reference to the example in FIG. 3, a pixel mapping pattern is selected at step 178. The pixel mapping pattern can be the same as that selected in step 168 in FIG. 10, wherein a unique light valve pixel $(i, j)_{lv}$ is turned to the ON state (or OFF state); while other light valve pixels are turned to the OFF state (or the ON state). The pixel mapping pattern is then produced by the light valve pixels and captured by the detector pixels (step 180). Based upon the captured pixel mapping pattern, which has one unique pixel, the detector pixel $(i, j)_{im}$ capturing the unique image pixel can then be identified (step 182); and such detector pixel is then correlated to the unique image pixel (also the light valve pixel generating the unique image pixel) at step 184. After correlating the light valve pixel $(i, j)_{lv}$ with detector pixel $(i, j)_{im}$, the remaining light valve pixels in the group of $G(i, j)_{lv}$ are searched and correlated to the detector pixel $(i, j)_{im}$, which starts from step 186.

At step 186, a new pixel mapping pattern is selected. This new pixel mapping pattern comprises light valve pixels $(i, j)_{lv}$ and an adjacent light valve pixel, such as $(i-1, j)_{lv}$ being turned to the ON state (or the OFF state); while the remaining light valve pixels are turned off (or on). The new pixel mapping pattern is then produced by the light valve pixels, and captured by the detector pixels (step 188). The intensity of the captured new image by the detector pixels is then compared with the previous captured images (e.g. the image having the unique image pixel). If the intensity changes, for example, beyond a threshold, the adjacent light valve pixel $(i-1, j)_{lv}$ is in the group of $G(i, j)_{lv}$, and thus being added to the group of $G(i, j)_{lv}$ at step 190. If the intensity difference between the captured new image and the previous image is not beyond the threshold, the adjacent light valve pixel $(i-1, j)_{lv}$ is not in the group of $G(i, j)_{lv}$. The above process is then reiterated by selecting new adjacent light valve pixels from all possible directions (e.g. along the row and columns), such as light valve pixel $(i+1, j)_{lv}$, $(i, j-1)_{lv}$, and $(i, j+1)_{lv}$, until all light valve pixels in the group of $G(i, j)_{lv}$ are identified and correlated to the detector pixel $(i, j)_{im}$ step 192. It is noted that a light valve pixels in the group of $G(i, j)_{lv}$ may or may not be in a square sub-array, as schematically illustrated in FIG. 3. In other examples, the light valve pixels in the group of $G(i, j)_{lv}$ can have other shapes, such as being in a rectangular sub-array with the length along the columns or rows.

Referring again to FIG. 9, if it is determined that a group mapping is not proper at step 162, an irregular pixel mapping can be performed at step 166. An irregular pixel mapping is preferred especially when the physical configurations of the light valve pixels and the detector pixels do not match, such as those illustrated in FIG. 5, FIG. 6, and FIG. 7. The irregular pixel mapping can be performed in many ways, one of which is demonstrated in the flow chart in FIG. 12.

Figure 12:
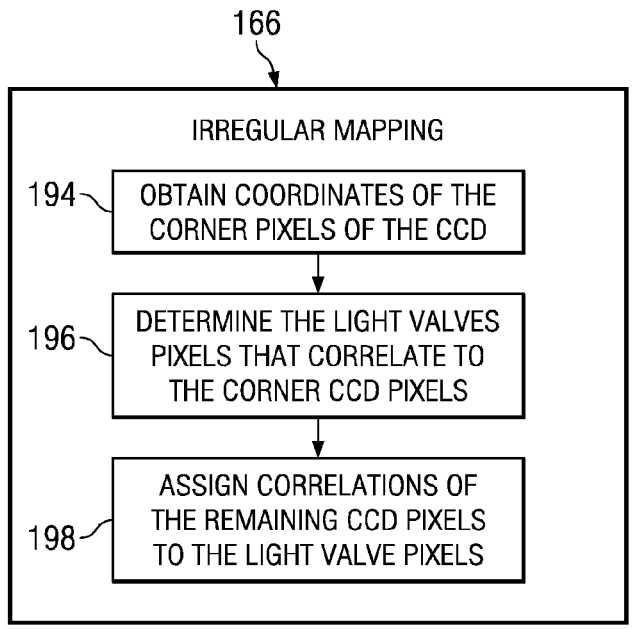
FIG. 12 is a flow chart showing the steps executed for performing an exemplary irregular pixel mapping in the method of FIG. 9.

Referring to FIG. 12 and as with reference to FIG. 6, an exemplary method for correlating a detector pixel array with a non-matching light valve pixel array is demonstrated. The method correlates the corner pixels or boundary pixels of the detector array with the light valve pixels. Based upon the above correlation and the physical configurations of the pixel arrays, correlations between the detector pixels and light valve pixels can be assigned. As a way of example wherein the detector array is an one row array comprising pixels of $(1, 1)_{im}$, $(1, 2)_{im}$, $(1, 3)_{im}$, and $(1, 4)_{im}$; and the light valve pixel is a one row array comprising pixels of $(1, 1)_{lv}$, $(1, 2)_{lv}$, and $(1, 3)_{lv}$. The correlation method correlates the corner pixels, i.e. detector pixels $(1, 1)_{im}$ and $(1, 4)_{im}$ to the detector pixels $(1, 1)_{lv}$, and $(1, 3)_{lv}$, respectively. The remaining detector pixels $(1, 2)_{im}$ and $(1, 3)_{im}$ are assigned to be correlated with the remaining light valve pixel $(1, 2)_{lv}$. The flow chart in FIG. 12 summarizes the above method.

At step 194, coordinates (e.g. the row and column indices) of the corner (or at the boundary) of the detector pixel array are obtained. Based upon the obtained coordinates and the physical configuration of the light valve pixel array, the corner pixels (or boundary pixels) of the detector are correlated with the corner pixels (or boundary pixels) of the light valve at step 196. Based on the correlations between the corner pixels (or boundary pixels) between the detector pixels and the light valve pixels, correlations between the remaining detector pixels and light valve pixels are assigned (step 198).

As discussed above with reference to FIG. 7, a detector pixel array can be correlated with the light valve pixels in a scaled correlation scheme. Specifically, a R×C detector pixel array can be correlated to a (p×R)×(q×C) sub-array of the light valve pixel array, while p and q are integers, and may or may not have the same value. This pixel mapping scheme, in fact, is applicable to any types of pixel arrays, regardless of the physical profiles of the pixel arrays. As a way of example, the above pixel mapping scheme can be used for mapping non-matching pixel arrays, as illustrated in FIG. 13.

Figure 13:
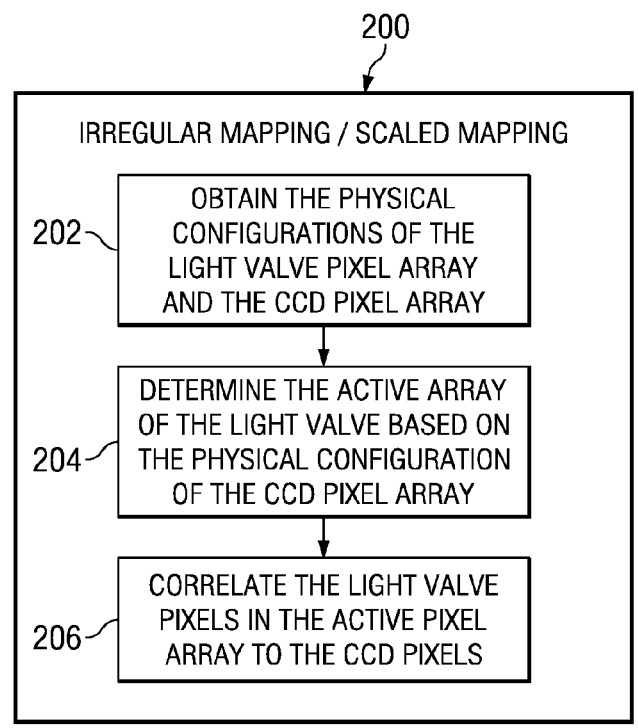
FIG. 13 is a flow chart showing the steps executed for performing another exemplary irregular pixel mapping in the method of FIG. 9.

Referring to FIG. 13 and as with reference to FIG. 7, physical configurations of the light valve pixel array and the detector array are obtained at step 202. Based upon the physical configurations, an active light valve pixel array (the sub-array) (p×R)×(q×C) is determined in the light valve M×N at step 204. The step 204 also determines integer parameters p and q. Pixels of the detector pixel array Rx C can then be correlated to the pixels in the sub-array (p×R)×(q×C) using a method as discussed above with reference to FIG. 11 or FIG. 12 or other pixel mapping methods.

Referring again to FIG. 1, with the above discussed pixel mapping scheme and pixel mapping methods, pixels of the light valve (104) and detector (212) of the image capturing unit (106) can be correlated. The correlation can be stored or maintained by the control unit (102). For example, the correlation can be stored as a look-up-table in storage medium; while the storage medium can be a functional member of the control unit, or can be a separate functional member from the control. In the later instance, the storage medium is connected to the control unit such that the control unit can retrieve the correlation from the storage medium during operations. With the correlation, the control unit is capable of controlling the light valve, as well as other necessary components, to produce image as desired locations. Depending upon the specific applications, the image system (100) in FIG. 1 can be implemented in many ways, one of which is schematically illustrated in FIG. 14.

Figure 14:
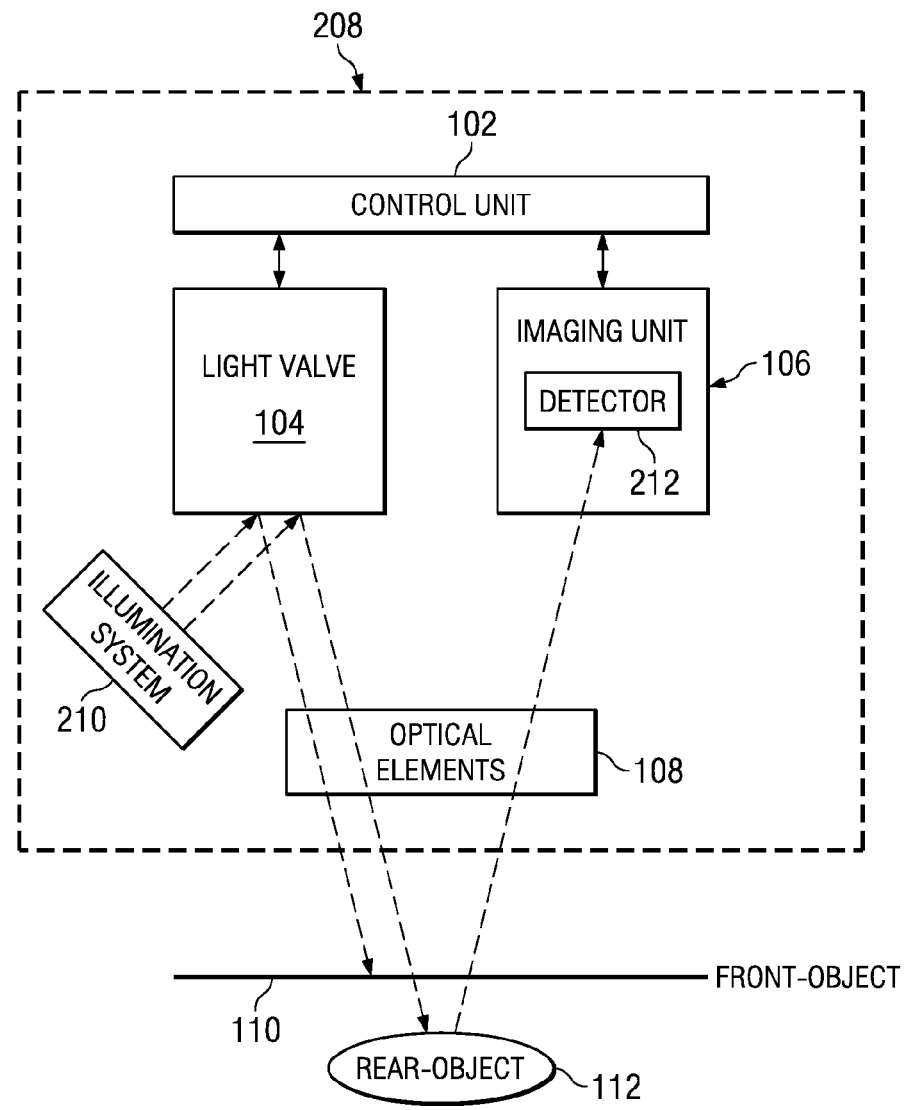
FIG. 14 is a block diagram illustrating an exemplary configuration of the image system in FIG. 1.

Referring to FIG. 14, light valve 104 in this example comprises an array of reflective pixels, such as reflective and deflectable micromirrors or LCoS devices. Producing images using a reflective light valve needs illumination light. As such, illumination system 210 is provided. The illumination system (210) comprises one or multiple light sources for providing light for capturing images of the object under test and producing images at desired images. Depending upon the specific application, the illumination system may comprise a wide range of different light sources. For example, when the image system (208) is designed to have the capability of detecting non-visible features and producing a visible image of the captured non-visible features, the illumination system (210) can comprise a light source emitting visible light and a light source emitting light capable of detecting the non-visible features. In particular, when the image system is desired to be capable of detecting subcutaneous features of a body part, an obscured structure embedded within or behind a wall, or features in the similar instances, infrared light can be used for these purpose. Accordingly, the illumination system comprises an IR source capable of emitting infrared light. In other applications, light other than visible light or infrared light can be used depending upon the native and methods of detecting the target feature to be captured. For example, the illumination system may comprise ultraviolet light that is to be used for treating affected portions of organs in mammal (e.g. human) bodies, which will be detailed afterwards. The light source(s) for emitting visible light in the illumination system can be any suitable light sources, such as arc lamps, solid-state illuminators (e.g. light emitting diodes, Asynchronous Spontaneous Emission (ASE) Sources, Quantum Dot sources, fiber amplifiers, fiber lasers, OLEDs and lasers as single, multiple or array emitters), and other types of light sources, such as ultraviolet light sources.

In correlating the pixels of the light valve (104) and detector 212, the light source(s) emitting light capable of being captured by the detector pixels is turned on; and the such light is projected to the target (e.g. the rear-object or the front project) through the light valve pixels so as to form the pixel mapping pattern. The pixel mapping pattern is then captured by the detector of the image capturing unit followed by pixel correlation as discussed above.

After the correlation of the light valve pixel and detector pixels, the light valve pixels can then be used to produce images, especially the captured images by the detector pixels, onto a display target (e.g. front-object 110) during an image producing process.

Figure 15:
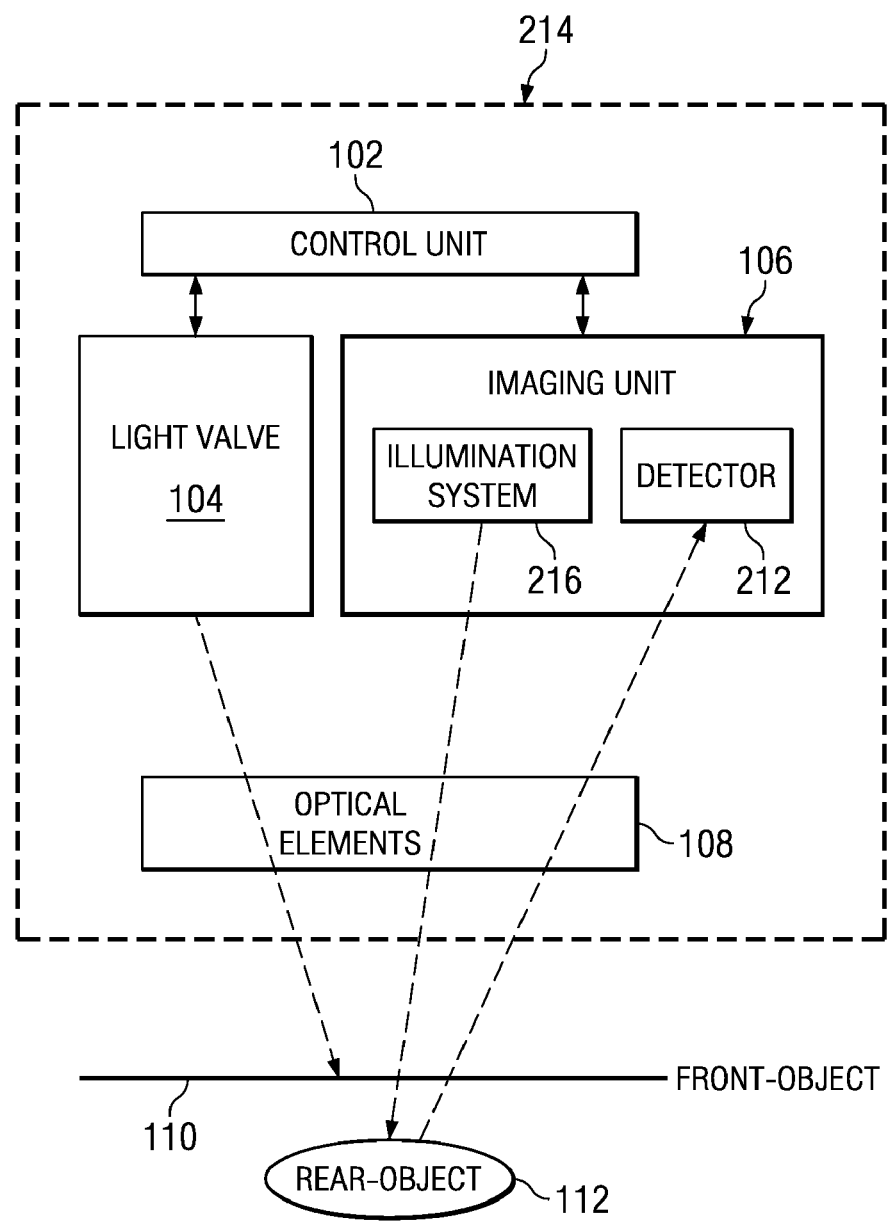
FIG. 15 is a block diagram illustrating another exemplary configuration of the image system in FIG. 1.

Instead of providing the illumination system as a separate module for illuminating the target object through the light valve pixels as illustrated in FIG. 14, the illumination system can be implemented as a module of the image capturing unit, as schematically illustrated in FIG. 15. This configuration can be of more importance when the light valve pixels are self-light emitting devices, such as plasma cells, Lasers, LEDs, ASE Sources, Quantum Dot sources, fiber amplifiers, fiber lasers OLEDs, all as single, multiple or array emitters, or other type of illuminators, in which instance, producing images by the light valve pixels may not need external illumination.

Referring to FIG. 15, illumination system 216 is a member of image capturing unit 106 that further comprises detector 212. In this example, the illumination system may comprise light sources emitting light that is capable of being captured by the detector pixels, such as infrared light. Because the light valve pixels are self-light emitting pixels, it is not necessary for the illumination to include light sources emitting visible light as that in FIG. 14.

In the process of pixel correlation, the light sources of the illumination system can all be turned off. The light valve pixels produce a selected pixel mapping pattern onto a target (e.g. front object 110) such that the mapping pattern can be captured by the detector (212) of the image capturing unit (106). Based upon the captured pixel mapping pattern, pixels of the detector and the light valve can then be correlated using a method as discussed above.

In the process of feature detection and image reproduction processes, the light source(s) of the illumination system can be turned on so as to illuminate the target (e.g. non-visible feature of rear-project 112). An image (e.g. a non-visible image) of the illuminated target is then captured by the detector. With reference to the obtained correlation, the light valve pixels can be used to generate a visible image of the non-visible features captured by the detector pixels; and produce the generated visible image at a desired location, such as a location on the front object (110) and aligned to the non-visible features of the rear-object 112.

The image capturing and image reproducing processes all may involve optical elements (108) as illustrated in FIG. 1, FIG. 14, and FIG. 15. The optical elements can be distributed in the image system in many ways to maximize the optical efficiency and performance of the image system. For example, the optical elements, as well as other system components can be deployed in the image system so as to form an off-axis optical system (as illustrated in FIG. 16) or an on-axis optical system (as illustrated in FIG. 17).

Figure 16:
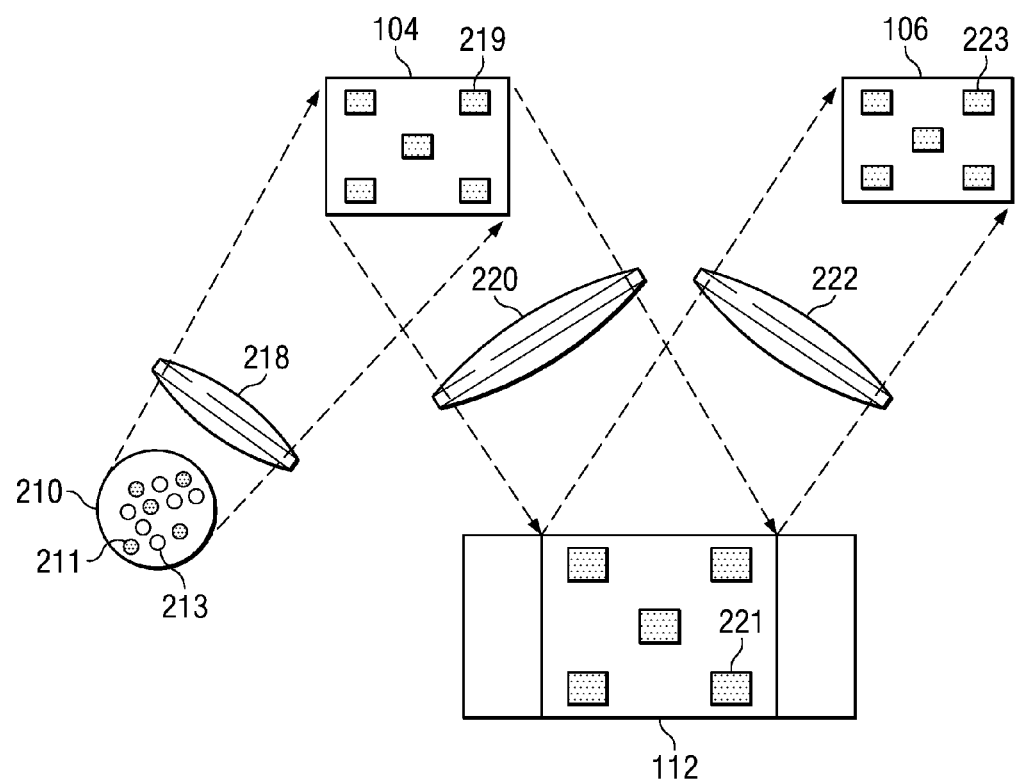
FIG. 16 is a block diagram demonstrating an exemplary method of correlating pixels of the light valve with pixels of the detector in the image capturing device of the image system with the configuration as illustrated in FIG. 14.

Referring to FIG. 16, an exemplary off-axis optical system configuration of the image system in FIG. 14 is schematically illustrated therein. In this exemplary configuration, illumination system 210 comprises light sources 211 and 213. Light source 211 emits light that is capable of illuminating non-visible features, such infrared light capable of illuminating subcutaneous features or internal organs of body parts. Light source 213 emits visible light, such as green, red, blue, and any combinations thereof. The illumination system may comprise any suitable number of light sources of the same kind so as to increase the illumination intensity. The light sources in the illumination system can be physically arranged in any desired ways, such as in-line arrangements, matrix-arrangements, and random arrangements. For increasing the optical efficiency, other optical elements can be provided. For example, optical fibers, light pipes, optical filters, transmissive lenses, and optical beam-shaping elements, such as fly-eye lenses can also be included in the illumination system. When the system is desired to have the capability of medical treatment using specific light, such as ultraviolet light and lasers, light sources of such specific light can be included, even though not required, in the light source (210).

Optical element 218, such as a condensing lens and/or lightpipe, is disposed in optical path to deliver light from the light source(s) to the light valve pixels (104). By setting the light valve pixels to proper states, selected images, such as a selected image pixel mapping pattern (219) and captured images by the detector pixels can be produced. The light incident to the light valve pixels is reflected to the target (e.g. non-visible feature 112) through optical element 220 (e.g. a projection optics) so as to illuminate the target, such as pixel mapping pattern 221 on non-visible feature 112. The so produced image on the target is then captured by the detector (106) through optical element 222, such as an optical lens. As such, the pixel mapping pattern and/or the image (223) of the non-visible features can be captured by the detector pixels. For simplicity purpose, some system components are not illustrated in FIG. 16, such as the control unit and communications between the control unit and the light valve and the image capturing unit. However, it will be appreciated by those skilled in the art that the image system may comprise any components usable for digital image capturing and digital image producing.

Figure 17:
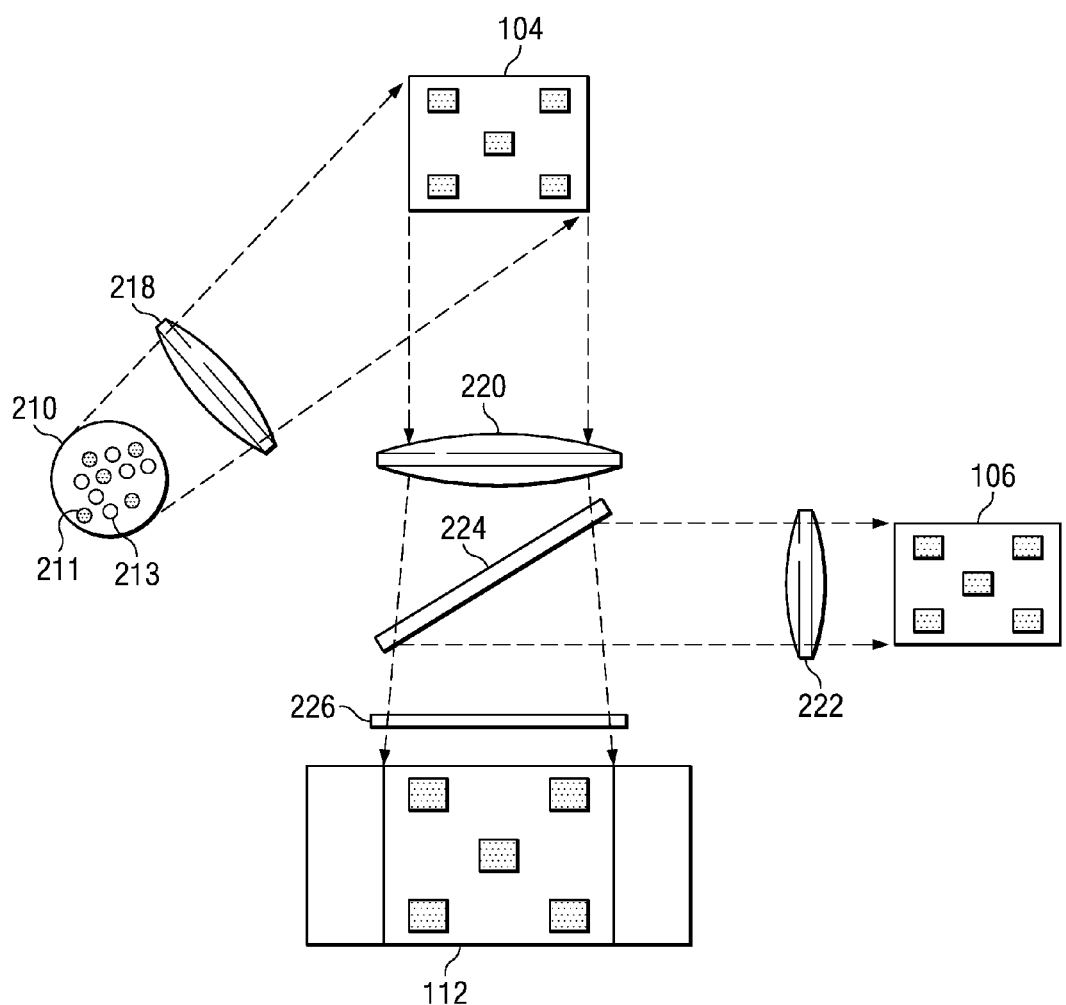
FIG. 17 is a block diagram demonstrating another exemplary method of correlating pixels of the light valve with pixels of the detector in the image capturing device of the image system with the configuration as illustrated in FIG. 14.

As an alternative to the off-axis optical system configuration, the image system of FIG. 14 can be configured to an on-axis optical system, an example of which is schematically illustrated in FIG. 17.

Referring to FIG. 17, illumination system 210 is provided, which can be the same as the illumination system in FIG. 16. The light from the illumination system is directed to the pixel array of light valve 104 through optical element 218. The light from the light valve pixels is directed to the target (112) through optical lens 220, hot-mirror 224, and quarter-wave plate 226. The hot mirror (224) can be any suitable hot mirrors depending upon the light system for capturing and reproducing images. For example, when visible light and infrared light are used, the hot mirror (224) can be a infrared hot mirror that is capable of reflecting light with wavelengths equal to or longer than infrared light; while passing light with shorter wavelengths, such as green light. In an alternative example, the hot mirror (224) can be replaced by a polarizing beam splitter followed by a quarter-waver plate or similar optical element (or combinations of optical elements) so as to allow initial passage of light to the target object and then reflectance to the detector of the image capturing unit. The light reflected from the target object (112) is guided toward detector 106 by quarter-wave plate 226, hot mirror 224, and optical lens 222 so as to be captured by the detector pixels.

It will be appreciated by those skilled in the art that the image systems as illustrated in FIGS. 16 and 17 are two of many possible exemplary implementations of the image system in FIG. 1 and FIG. 14. The image systems in FIG. 16 and FIG. 14 each may comprise other functional members, such as optical filters, transmissive lenses, specular or non-specular folding mirrors, diffractive optical elements, light guides, and other related imaging processing components.

The image systems as discussed above, as well as other variations within the scope of this disclosure, have a wide range of applications. For example, the image system can be used for producing images that are captured by the detector of the image capturing unit of the system at desired locations, an exemplary method of which is demonstrated in the flow chart in FIG. 18. As mentioned earlier herein, this method can be useful in producing a visible image of a non-visible feature at a location that is aligned to the non-visible features. This method can also be useful in camouflaging a visible object by producing a background image onto the visible surface of the object to be camouflaged. Of course, the method is also useful for many other applications.

Figure 18:
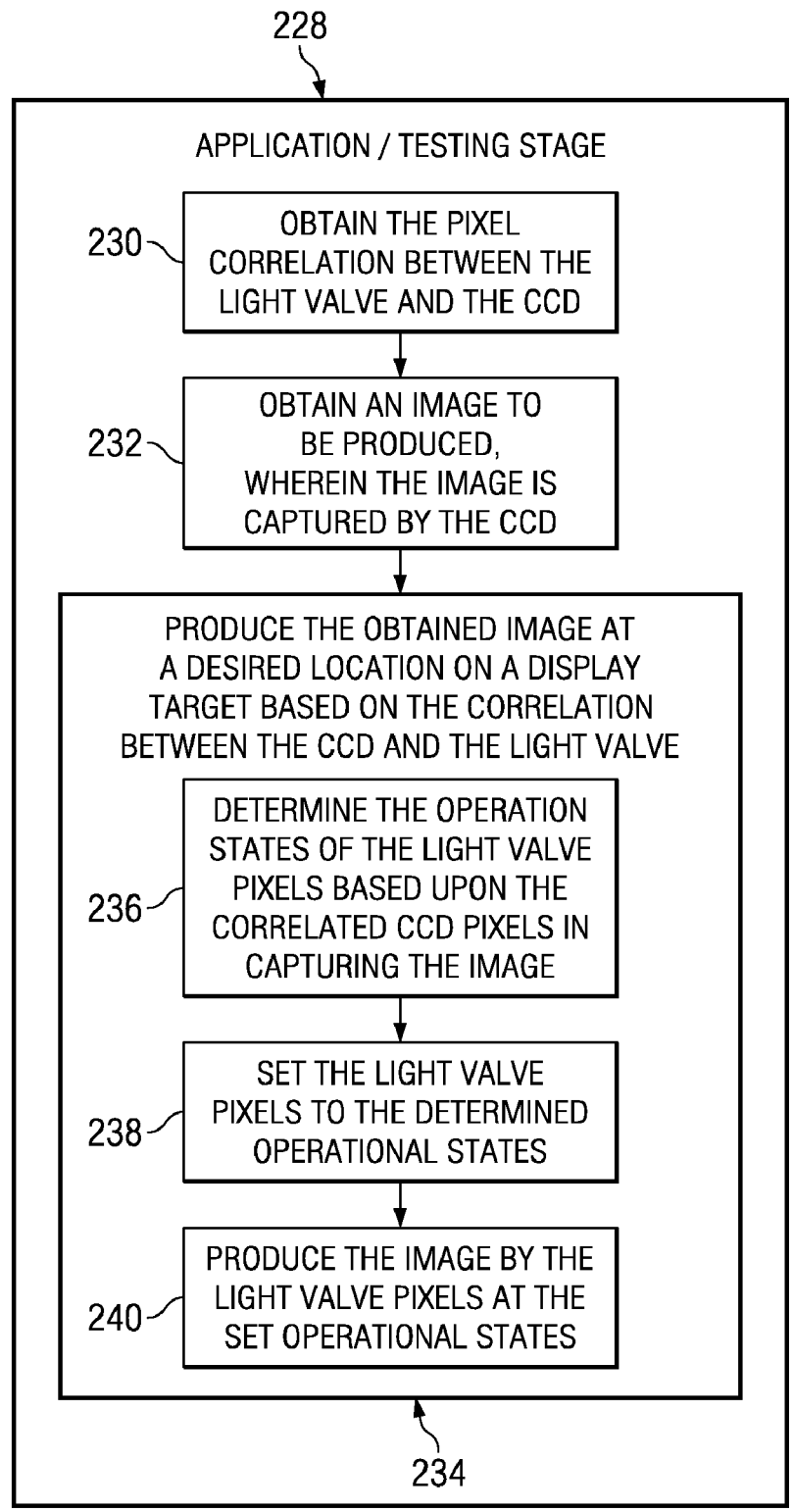
FIG. 18 is a flow chart showing the steps executed for performing a method of producing a captured image at a desired location of a display target.

Referring to FIG. 18, the pixel correlations between the light valve pixels and detector pixels are retrieved, for example, by the control unit (102 in FIG. 1) of the image system at step 230. The correlation can be stored and retrieved as a look-up-table or other suitable forms. An image captured by the detector and to be produced by the image system is obtained at step 232. The obtained image is then produced by the light valve pixels based on the retrieved correlation at step 234. The image producing step 234 may further comprise a step (236) of determining the operational states of the light valve pixels based on the correlations and the image to be produced. For example, when image pixel $(i, j)_{im}$ of the image to be produced has a relative value of 100% of the maximum pixel intensity of the image, the light valve pixel $(i, j)_{lv}$ correlated with the image pixel $(i, j)_{im}$ is set to the ON state (or the OFF state). When image pixel $(i, j)_{im}$ of the image to be produced has a relative value between 0% and 100% (e.g. 70%) of the maximum pixel intensity of the image, a pulse-width-modulation technique can be used to simulate the gray-scale. Specifically, the light valve pixel $(i, j)_{lv}$ correlated with the image pixel $(i, j)_{im}$ can be set to a sequence of ON and OFF states during a certain time period, such as a frame period. As a consequence, the collective visual effect of the light from the light valve pixel $(i, j)_{lv}$ appears to have an intensity that is substantially equal to the desired percentage of the maximum intensity of the produced image, such as 70% of the full white (or full black) that can be produced by the light valve pixels. Of course, the intensity percentage of the light from light valve pixel $(i, j)_{lv}$ can also be the percentage of the original detector pixel $(i, j)_{im}$ that was used in capturing the light.

After the state determination at step 236, the light valve pixels are set to the determined states (step 238) followed by producing the image by the light valve pixels at a desired location (step 240).

As can be seen from the above, because the detector pixels are correlated to the light valve pixels, and the states of the light valve pixels in producing the captured image are determined by the outputs or values of the correlated detector pixels in capturing the image, the produced image by the light valve pixels is in fact, a reversion of the captured image at the desired location. However, light of one wavelength (or waveband) that is suitable for detecting the target features can be used for detecting the target features; while light with another wavelength (or waveband), such as light that is more suitable for human visualization can be selected for producing the image. Moreover, by fixing the relative positions of the light valve pixels and detector pixels during the image capturing and image producing, the image can be produced at a location that is substantially aligned to the object, from which the image to be produced is captured. Specifically, during one operation that comprises an image capturing using the detector and an image producing using the light valve, the relative positions of the light valve pixels and the detector pixels are preferably kept constant. The relative positions of the light valve pixels and the detector pixels, however, can be changed as desired between two separate operations.

Figure 19:
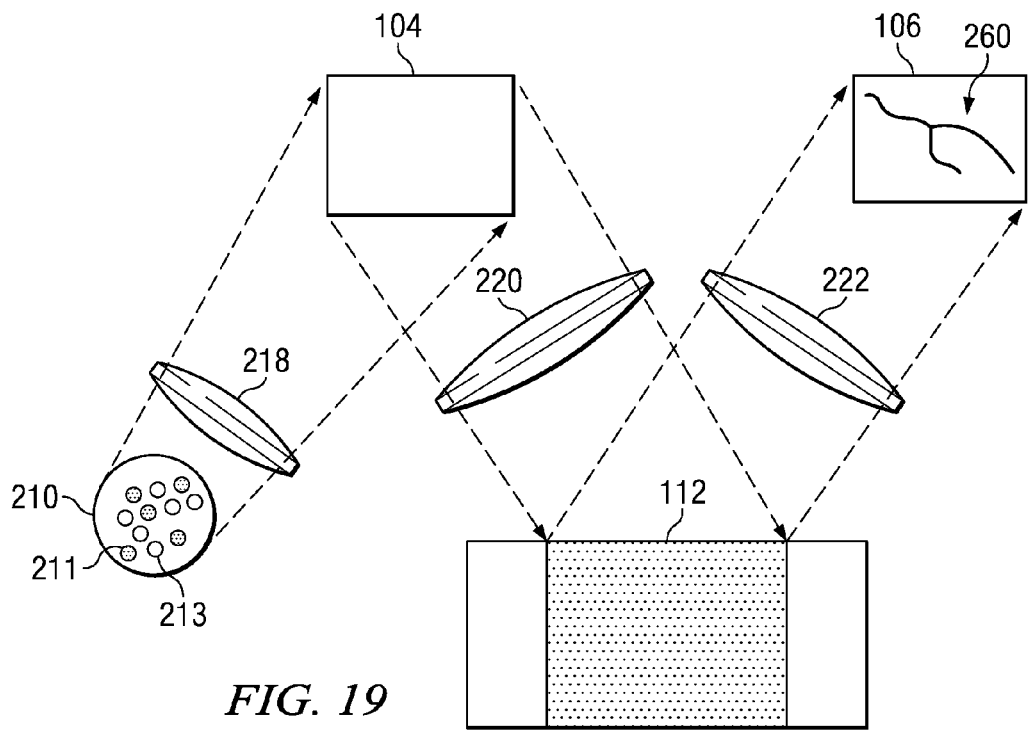
FIG. 19 is a block diagram demonstrating a method of detecting a non-visible feature using the image system in FIG. 1.

For demonstration purpose, FIG. 19 schematically illustrates an exemplary application for detecting a non-visible subcutaneous feature, such as veins, of a body part, such as human arm.

Referring to FIG. 19, subcutaneous feature 112 is non-visible by visible light, but can be detected by infrared light. For this reason, illumination system 210 comprises IR light source 213 that is capable of emitting infrared light. For producing visible images by reflective pixels (e.g. reflective and deflectable micromirrors and LCOS) of the light valve (104), the illumination system (210) further comprises light source 211 capable of emitting visible light, such as green light.

For detecting the subcutaneous feature 112, infrared light is generated by the illumination system and directed to the light valve pixels through optical element 218. The pixels of light valve (104) reflect the infrared light onto the subcutaneous features through optical element 220 so as to illuminate the subcutaneous features. In the example as illustrated in FIG. 19, substantially the entire area of the subcutaneous feature (112) is illuminated by the infrared light from the light valve pixels. The subcutaneous feature absorbs a portion of the incident infrared light and reflects the remaining For example, blood vessels absorb the incident infrared light more, and reflect less than the surrounding subcutaneous fat and tissues. As a consequence, the reflected infrared light from the body part under test has an intensity distribution. The reflected light with less intensity corresponds to the blood vessels; while the reflected light with higher intensities corresponds to subcutaneous fat and tissues. Therefore, the light intensity distribution corresponds to the invisible feature under test, and can thus be used for deriving the geometric image of the invisible feature. By capturing the reflected light from the body part under test (and through optical element 222) using pixels of detector 106, an image (260) of the subcutaneous feature under test can be obtained. Image derivation from the light intensity (and the light intensity distribution) can be accomplished by an image processing unit of the system, wherein the image processing unit can be a member of the image capturing unit (106) or can be a member of the control unit (102) or can be a standalone unit of the system as schematically illustrated in FIG. 1. The image processing unit can be implemented as a standalone software module having computer-executable instructions or can be a dedicated electronic circuit. Regardless of different implementations, the image processing unit is connected to the detector of the image capturing unit and other suitable components of the system, such as the light valve such that the processed images can be properly stored and reproduced by the light valve of the system. When necessary, the image processing unit can be connected to a storage or image buffer in which the processed, unprocessed, or other related image processing signals (control and/or data signals) can be stored. In examples wherein the system is implemented to be capable of performing desired medical treatments, such as treating affected portions of human or mammal bodies using for example ultraviolet light or lasers, the image processing unit can be connected to the control unit (e.g. control unit 102 in FIG. 2) or a proper system component designated for performing the medical treatment.

The obtained image can then be reproduced at the surface of the body part under test and aligned to the subcutaneous feature using visible light and the light valve pixels. Specifically, the light source (e.g. light source 211) emitting visible light can be turned on. The visible light is directed to the light valve pixels through optical element 218 in the same way as the infrared light. The light valve pixels are individually set to states based on the correlations with the detector pixels and the outputs or values of the detector pixels in capturing the non-visible feature (260). With the set states, the light valve pixels individually reflects the incident light onto (in the ON state) or away from (in the OFF state) the surface of the body part under test. With such operation, the produced visible image corresponds to the image of the non-visible feature captured by the detector pixels, and is at a location aligned to the non-visible subcutaneous feature.

Figure 20:
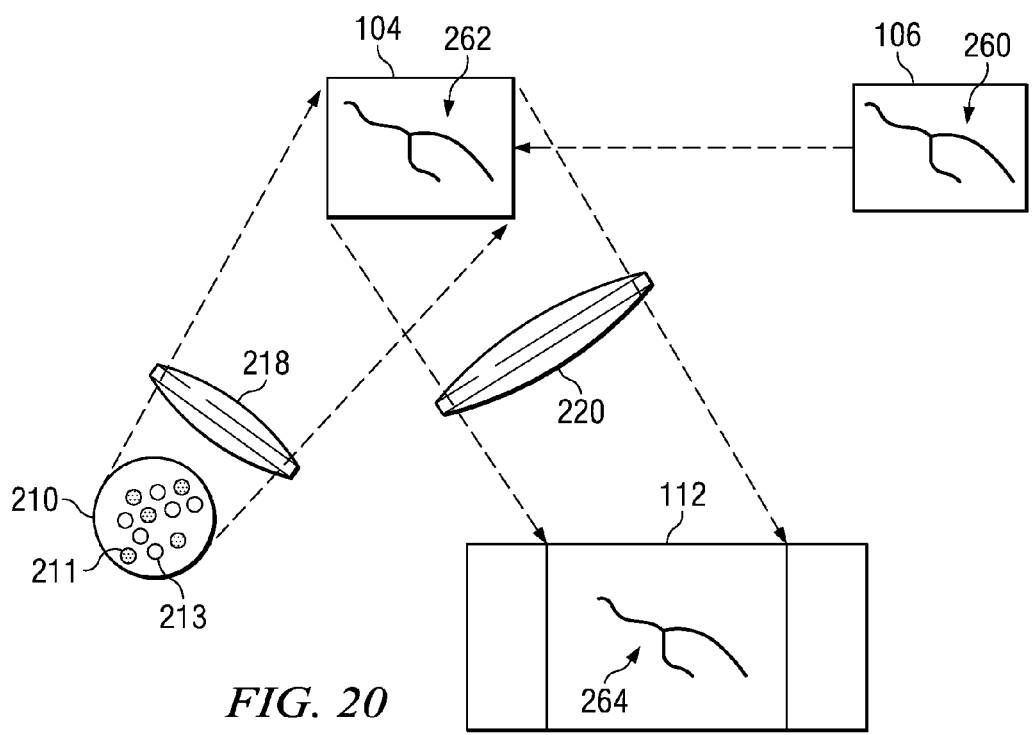
FIG. 20 is a block diagram demonstrating a method of projecting a visible image associated with a captured non-visible image at a desired location of a display target.

Another exemplary application for producing a visible image of a non-visible feature at a desired location is schematically illustrated in FIG. 20. Referring to FIG. 20, it is assumed that an image of a non-visible feature has been captured by the detector (106) using, for example, infrared light; and the correlations between the light valve pixels and the detector pixels have been determined. For reproducing the non-visible image of the non-visible feature with visible light and at the desired location, the light valve pixels are individually set to operational states (e.g. the ON and OFF states) based on the correlations and the non-visible image. The light valve pixels are then illuminated by visible light from the illumination system. The light valve pixels individually reflect the incident visible light onto (at the ON state) or away from (at the OFF state) surface 112 of the display target (e.g. the surface of the body part under test) so as to generate a visible image (264) of the non-visible image (260) captured by the detector (106).

Figure 21:
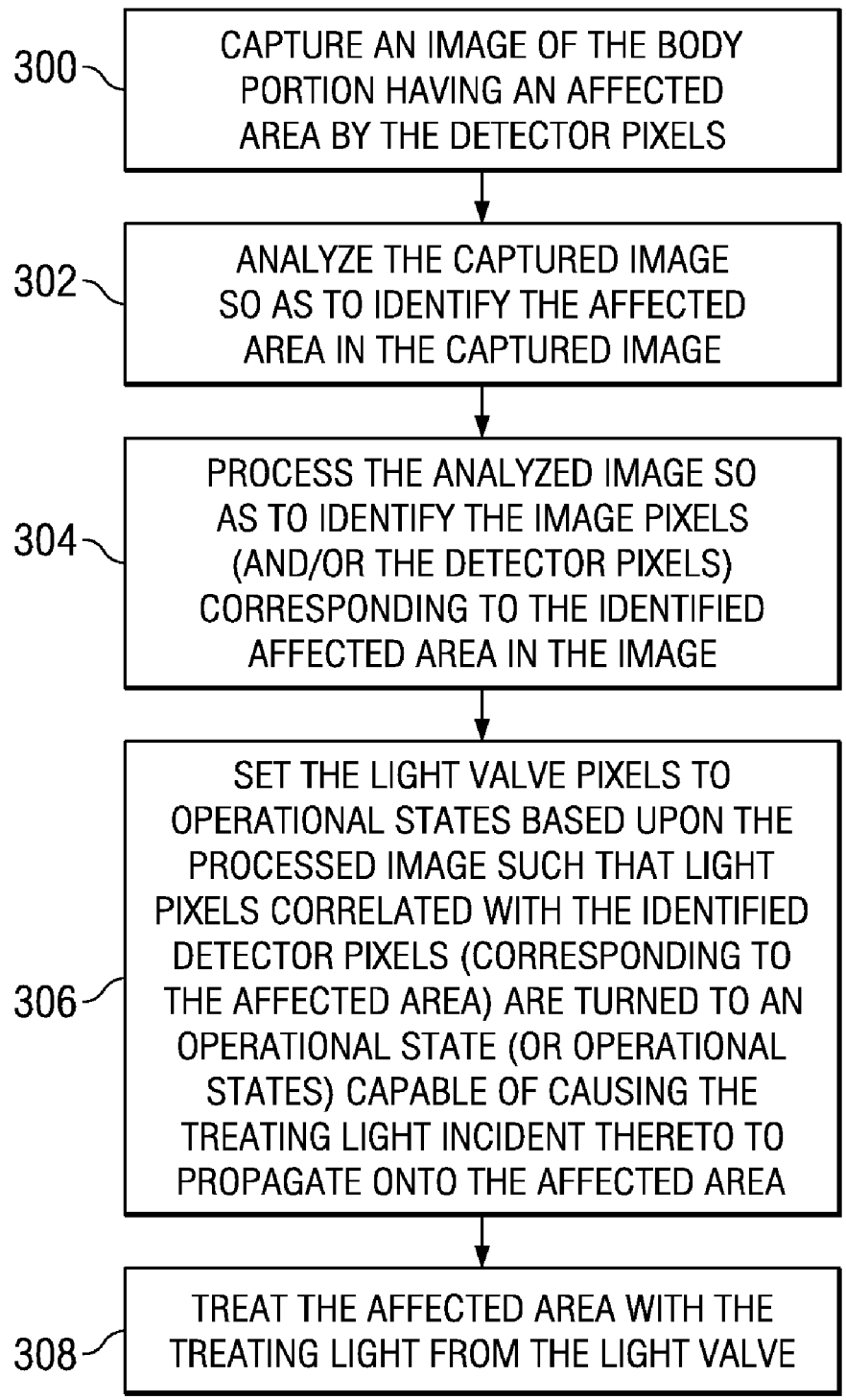
FIG. 21 presents a flow chart showing the steps executed for performing an exemplary medical treatment that does not require moving the selected treating light using the system.
Figure 22:
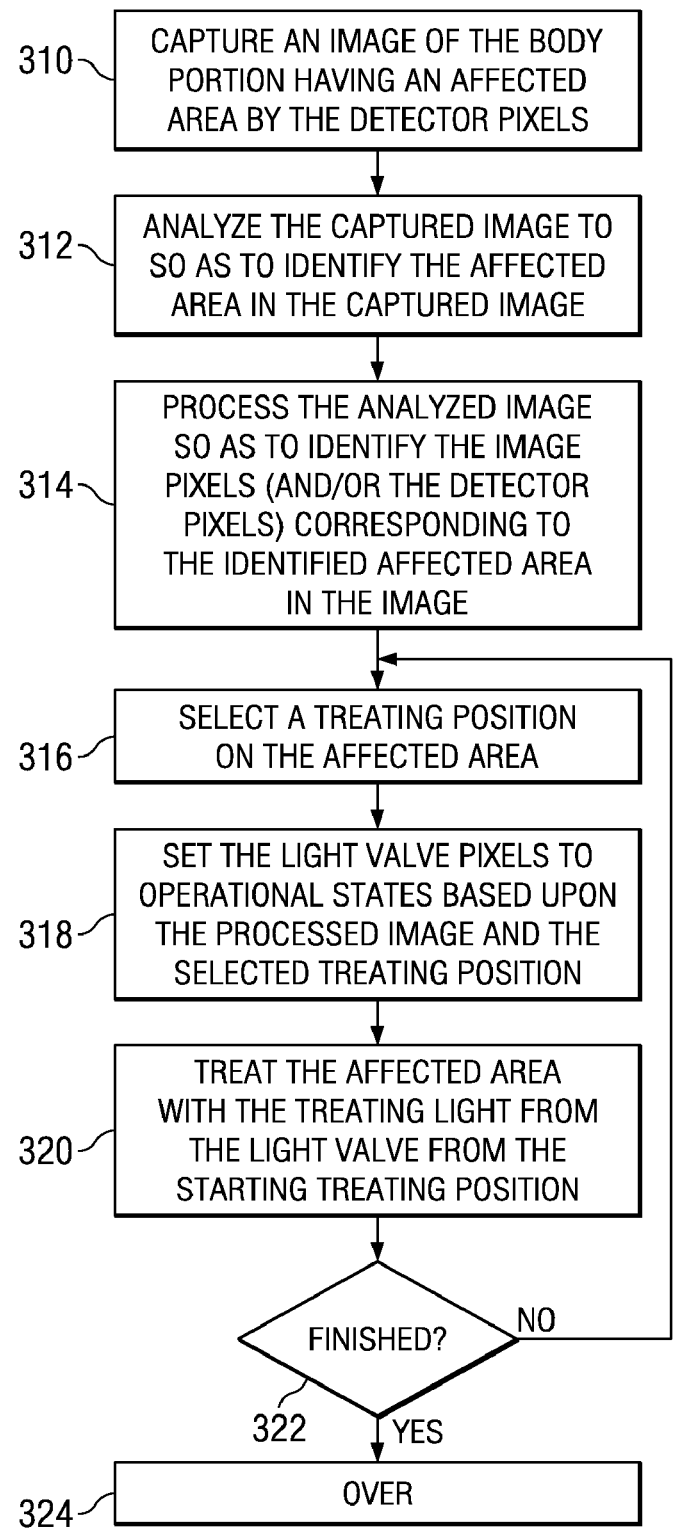
FIG. 22 presents a flow chart showing the steps executed for performing another medical treatment that require moving the selected treating light using the system.

Other than producing a visible image of an invisible feature at the location aligned to the location of the invisible feature, the light used for reproducing the image can be directly used for treating affected portion of a human or mammal body, in which instance, the light used for producing the image can be replaced by other suitable light, such as ultraviolet light. This method can be of great importance in medical treatment. As one example, ultraviolet light can be selected for treating skin conditions, such as psoriasis or vitiligo. In this example, the treating light (e.g. the ultraviolet light) is assumed to be capable of illuminating the entire affected area at each illumination treatment, regardless whether the affected area is visible or invisible. FIG. 21, which will be discussed in the following demonstrates the above exemplary treatment method. In another example, the target object to be treated with a selected light beam may be larger than the illumination area of the selected area. In particular when a laser beam is to be used for treating the affected area, or when a laser beam is to be used for treating or cutting the affected area, the selected light is desired to move to different positions at the affected area during the treatment; wherein such movement can be continuous or discrete. An exemplary method for such instance is illustrated in FIG. 22 and will be discussed in the following. It will be appreciated by those skilled in the art that the following examples as will be discussed with reference to FIGS. 21 and 22 are for demonstration purpose, and should not be interpreted as a limitation. The system and method are also applicable to other variations.

Referring to FIG. 21, an image of the body portion having an affected area is captured using the detector pixels at step 300. The affected area can be skin conditions, such as psoriasis or vitiligo, on a skin portion of a human body. In this instance, the image can be captured by the detector pixels using visible light. When the affected portion is invisible, such as underneath the skin, the image of the invisible body portion having the affected area can be captured using selected light, such as IR light as discussed above.

The captured image of the body portion is then analyzed at step 302 so as to identify the affected area in the body portion (step 302). Such analyzing step can be performed by an image processing unit of the system, and more preferably an image processing unit connected to an user interface, through which professionals (e.g. doctors) can interact with the image processing unit in identifying the affected area in the captured image.

The analyzed image can then be processed so as to identify the image pixels (and or the detector pixels) corresponding to the identified affected area in the image (step 304). Based upon the processed image (the identified detector pixels) and the correlation, light valve pixels are initialized. Specifically, light valve pixels corresponding to the identified detector pixels are set to an operational state (or operational states) such that the selected treating light (e.g. ultraviolet light) incident thereto can be directed to the corresponding affected area to be treated (step 306). Light valve pixels corresponding to the unaffected areas or areas not needing to be treated, are set to an operational state (or states) such that the selected treating light incident thereto is directed away from the body portion, especially when the selected light is dangerous to healthy human or mammal tissue. The selected treating light can then be directed to the affected area using the pre-set light valve pixels by for example, illuminating the selected treating light to the light valve pixels (step 308).

There exist examples wherein the illumination area of the selected light at the affected area is less than the affected area such that illuminating the affected area by the selected light is not sufficient to treat the entire affected area. There are also examples wherein lasers or other selected light beams are to be used for treating the affected area or even removing the affected area from the body portion. In favor of high accuracy of the operation, the selected light beam is preferred to have a small dimension (e.g. small far-field illumination area). In the above examples, it is desired that the selected treating light is movable across or around the affected area. An exemplary method capable of moving the treating light across or around the affected area is demonstrated in the flow chart in FIG. 22.

Referring to FIG. 22, an image of the affected area of a body portion in a patient or a mammal is captured at step 310. This image capturing step can be performed in the same way as step 300 in FIG. 21 regardless of the visibility or the location of the affected area of the body portion. The captured image is then analyzed at step 312 so as to identify the affected area in the captured image, which can be performed in the same way as step 302 in FIG. 21. The analyzed image can then be processed at step 314, which can be performed in the same way as step 304 in FIG. 21.

Based upon the analyzed image, a treating position is selected at step 316 because the medical treatment with the selected light is desired to be performed through multiple steps due to the smaller illumination area of the selected treating light as compared to the affected area. Based upon the selected treating position, the detector pixels corresponding to the image pixels of the selected treating position, and the correlation between the detector pixels and light valve pixels, the light valve pixels are pre-set (step 318) to their operational states such that, the treating light incident to the light valve pixels corresponding to the selected treating position can be directed to the selected treating position; while the treating light incident to other light valve pixels is preferably directed away from the affected area by the light valve pixels.

The selected treating light is then directed to the affected area from the pre-set light valve pixels, for example, by illuminating the light valve pixels with the selected treating light (step 320).

After completing the desired medical treatment at the selected treating position at step 320, it is determined if the entire affected area has been properly treated. If so, the treatment is finished at step 324. Otherwise, the method flow back to step 316 wherein a new treating position in the affected area is selected followed by resetting the light valve pixels (step 318). The new selected treating position is then treated properly at step 320. The above process repeats until the entire affected area of the body portion is properly treated.

Figure 23A:
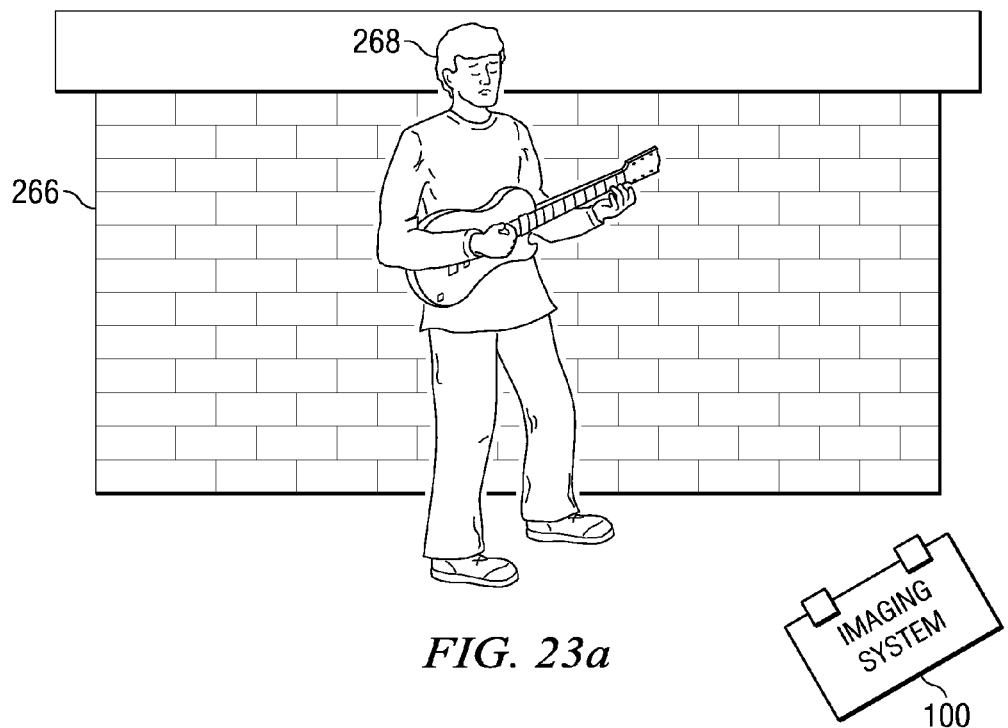
FIG. 23a and FIG. 23b schematically illustrate an exemplary method of camouflaging a visible object.
Figure 23B:
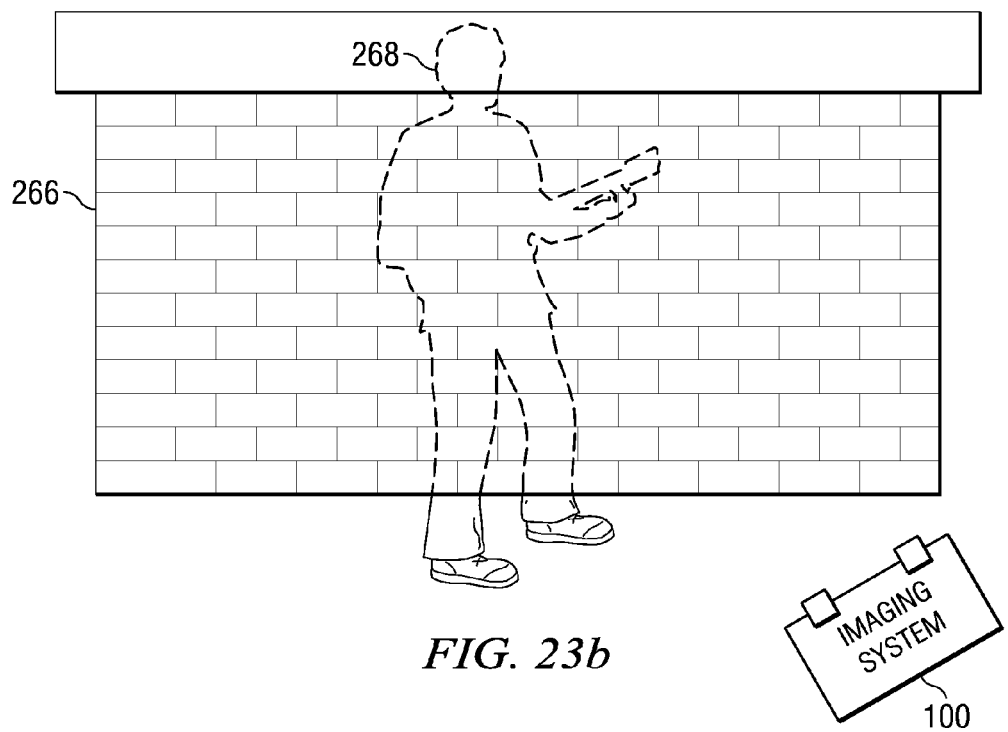

Instead of producing a visible image of a non-visible feature, the image system as discussed above can also be used for camouflaging a visible object, an exemplary method of which is schematically illustrated in FIG. 23a and FIG. 23b.

Referring to FIG. 23a, a visible object, such as a person (e.g. a military soldier or police person) 268, stands in front of a background, such as wall 266. For demonstration and simplicity purposes, it is assumed that the background (e.g. wall 266) and the soldier all are black-and-white. The soldier is visible because the soldier conceals a portion of the background wall; and human eyes perceive different intensities of light reflected from the soldier and the background. In other words, the light reflected from the soldier breaks the continuity of the background wall perceived by human eyes. For camouflaging the soldier (not perceivable by human eyes), an image of the concealed portion of the wall can be projected back onto the visible surface of the soldier so as to fix the discontinuity of the perceived image in human eyes. As a consequence, human eyes perceive a continuous background (wall), and the soldier can thus be camouflaged, as schematically illustrated in FIG. 23b.

For projecting the concealed portion of the background onto the corresponding visible surface of the soldier, image system 100 is provided. The image system (100) can be configured to the system as discussed above reference to 14. However, the illumination system may comprise light sources for visible light. In some examples, a light source for infrared or light of other wavelength ranges, can be included.

The detector of the image capturing unit can be disposed at a location for detecting the concealed portion of the background; and the light valve can be disposed at a location for projecting the captured image of the concealed portion back onto the corresponding visible surface of the soldier. In one example, the image system (100) can be held by the soldier. In another example, the light valve pixels can be self-light emitting pixels; and/or deployed on the visible surface of the soldier.

When the background and/or the object exhibit colors, an illumination system carrying light sources emitting colored light, such as red, green, blue, yellow, cyan, magenta, or any combinations thereof, can be provided. The above discussed image producing method can be extended to be operated on each color component of the captured image so as to generate a color image at the desired location.

It will be appreciated by those of skill in the art that a new and useful image system capable of capturing images and reproducing the captured images at desired locations, as well as methods of using the same, have been described herein. In view of the many possible embodiments, however, it should be recognized that the embodiments described herein with respect to the drawing figures are meant to be illustrative only and should not be taken as limiting the scope of what is claimed. Those of skill in the art will recognize that the illustrated embodiments can be modified in arrangement and detail. Therefore, the devices and methods as described herein contemplate all such embodiments as may come within the scope of the following claims and equivalents thereof.

We claim:

1. A method, comprising:
providing an image system that comprises a light valve and an image capturing unit that comprises a detector, wherein the light valve comprises an array of individually addressable pixels, and wherein the detector comprises an array of detector pixels;
obtaining a correlation between the light valve pixels and the detector pixels;
capturing an image using the detector pixels; and
reproducing the captured image using the light valve pixels based on the obtained correlation and the captured image;
wherein the step of capturing an image further comprises:
directing non-visible light to the light valve pixels;
reflecting the non-visible light by the light valve pixels onto a non-visible feature;
capturing, by the detector pixels, light from the non-visible light so as to generate an image of the non-visible feature by the detector pixels;
setting each light valve pixel to a state based on a state of the correlated detector pixel when said detector pixel is capturing the light from the non-visible feature; and
producing a visible image by the light valve pixels.

2. The method of claim 1, wherein the captured image is a non-visible image of the non-visible feature; wherein the reproduced image is a visible image of the non-visible feature; wherein the reproduced visible image is at a location substantially aligned to the location of the non-visible feature.

3. The method of claim 1, wherein the step of producing a visible image by the light valve pixels further comprises:
directing visible light to be incident on the light valve pixels; and
reflecting the incident visible light by the light valve pixels so as to generate the visible image.

4. The method of claim 1, wherein the step of obtaining a correlation between the light valve pixels and the detector pixels further comprises:
correlating each detector pixel with one or a group of light valve pixels.

5. The method of claim 4, further comprising:
providing light that is capable of being detected by the detector pixels;
selecting a pixel mapping pattern;
producing the pixel mapping pattern at a location that can be detected by the detector, comprising:
- directing the provided light to the light valve pixels that are reflective pixels; and
- producing the pixel mapping pattern by the light valve pixels using the provided light;

capturing the produced pixel mapping pattern by the detector; and
correlating the detector pixels with the light valve pixels based on the captured pixel mapping pattern.

6. The method of claim 1, wherein the detector pixel array has a resolution different from a resolution of the light valve pixel array.

7. The method of claim 1, wherein the each detector pixel is correlated to a sub-array of light valve pixels.

8. The method of claim 1, wherein the light valve pixels are reflective pixels or self-light emitting pixels.

9. The method of claim 8, wherein the light valve pixels are reflective and deflectable micromirrors or liquid-crystal-on-silicon cells.

10. The method of claim 1, wherein the captured image is part of a medical treatment.

* * * * *